United States Patent
He et al.

(10) Patent No.: US 8,598,128 B2
(45) Date of Patent: Dec. 3, 2013

(54) FRUCTOSYLATED PUERARIN, AND PREPARATION METHOD AND USE THEREOF

(76) Inventors: Bingfang He, Jiangsu (CN); Xueming Wu, Jiangsu (CN); Jianlin Chu, Jiangsu (CN); Bin Wu, Jiangsu (CN); Sen Zhang, Jiangsu (CN); Pingkai Ouyang, Jiangsu (CN)

( * ) Notice: Subject to any disclaimer, the term of this patent is extended or adjusted under 35 U.S.C. 154(b) by 0 days.

(21) Appl. No.: 13/820,522

(22) PCT Filed: Sep. 23, 2011

(86) PCT No.: PCT/CN2011/001618
§ 371 (c)(1),
(2), (4) Date: Apr. 7, 2013

(87) PCT Pub. No.: WO2012/048522
PCT Pub. Date: Apr. 19, 2012

(65) Prior Publication Data
US 2013/0190266 A1    Jul. 25, 2013

(30) Foreign Application Priority Data

Oct. 13, 2010  (CN) .......................... 2010 1 0511959
May 10, 2011  (CN) .......................... 2011 1 0119350

(51) Int. Cl.
A61K 31/70    (2006.01)
A61K 31/715   (2006.01)
C07H 15/00    (2006.01)
C07H 17/00    (2006.01)

(52) U.S. Cl.
USPC ....... 514/27; 514/53; 514/61; 536/8; 536/123

(58) Field of Classification Search
None
See application file for complete search history.

(56) References Cited

PUBLICATIONS

Li et al., Carbohydrate Research, vol. 339, 2004, pp. 2789-2797.*

* cited by examiner

*Primary Examiner* — Traviss C McIntosh, III
(74) *Attorney, Agent, or Firm* — George G. Wang; Bei & Ocean

(57) ABSTRACT

Fructosylated puerarin being converted from puerarin by a bioconversion method conducted in an aqueous phase or non-aqueous phase system, including monofructosyl-(2,6)-puerarin, bifructosyl-(2,6)-puerarin, trifructosyl-(2,6)-puerarin, tetrafructosyl-(2,6)-puerarin and pentafructosyl-(2,6)-puerarin. Tests have shown that the oligosaccharylated puerarin is effective to treat acute myocardial ischemia, and can markedly suppress in vitro the proliferation of human breast cancer cell strain MDA-MB-23 and human chronmyelogenors leukemia cell strain K562, and it has a low toxicity.

19 Claims, 16 Drawing Sheets

FRUCTOSYLATED PUERARIN, AND PREPARATION METHOD AND USE THEREOF

CROSS-REFERENCE TO RELATED APPLICATIONS

This application claims priority from PCT Application No. PCT/CN2011/001618, filed Sep. 23, 2011, CN Application No. 201010511959.3, filed Oct. 13, 2010, and CN Application No. 201110119350.6, filed May 10, 2011, the contents of which are incorporated herein in the entirety by reference.

FIELD OF THE INVENTION

The present invention relates to the field of bio-pharmaceutical technology and, more specifically, to new derivatives of puerarin and their associated biological conversion methods and pharmaceutical applications.

BACKGROUND OF THE INVENTION

Puerarin is extracted from puerarialobata (Willd.) Ohwi and P. thomaonii Benth, and is isoflavonoid C-glycosides with the chemical name 7,4'-dyhydroxy-8-β-D-glucosyl isoflavone, appearing as a white needle shaped crystal. It is dissolvable in water, but with a low solubility (6.24 g/L), and its water solution is colorless or slightly yellow. Its molecular weight is 416.37. Puerarin is one of the main active components in the traditional Chinese medicine Radix Puerariae, a natural low toxicity and effective medicine for treating cardio-cerebral vascular system diseases, with extensive pharmacological action. It has been clinically used to reduce blood pressure, slow down heart beat rate, and lower myocardial oxygen consumption. It can dilate coronary arteries and improve the metabolism of normal and ischemic myocardium. It has effect on cerebral circulation, peripheral vascular and micro-circulation. In addition, puerarin has the effects of controlling the blood sugar level, and anti-oxidation and anti-tumor (Yao Dan and Ding Xiansheng, Chinese Journal of Clinical Pharmacology and Therapeutics, 2008, 13, 468-474.).

At present, puerarin formulations include liquid injection, eye drops and lyophilized powder injection, and in actual clinical application, it is mainly administered by injection (Wu Yanhong, Su Ziren, Lai Xiaoping, et la. Traditional Chinese Drug Research & Clinical Pharmacology, 2004, 15 (4): 259-261.). As the solubility of puerarin in water is low, in clinical application, a cosolvent is required to raise the solubility. In the present time, a high concentration of propylene glycol is normally added as the cosolvent, thereby not only increasing the cost, but also making filtration more difficult in production due to a high viscosity. Furthermore, it reduces safety and performance of the medicine due to increased contents of insoluble impurity, causing some toxic side effect to human body. Thus, for making it more convenient in use, there is a need to improve the solubility and bioavailability of puerarin. According to relevant literatures, the main methods used today include glycosylation of puerarin or using a special formulation to effectively improve the puerarin solubility. Up to date, the reports on glycosylation of puerarin include the following: Li et al (Li D, Park S H, Shim J H, et al. Carbohyd Res, 2004, 339, 2789~2797.) in 2004 first reported glycosylating puerarin using in vitro enzyme method, glucosyl-α-(1,6)-puerarin (CASRN: 824959-75-3) and maltosyl-α-(1,6)-puerarin (CASRN: 824959-76-4) of glycosyl substitute on C-6" hydroxyl group was obtained by catalytic composition of maltogenic amylase originated from bacillus thermophilus. The catalytic reaction took place with 1% (w/v) puerarin and 3% (w/v) soluble starch as the glycosyl donor, for 45 min at 55° C., and the product yield was 70%. Both converted products were separated and purified by a preparative HPLC method, and their water solubility was increased by respectively 14 times and 168 times as compared with puerarin. Jiang Jierong et al (Jiang J R, Yuan S, Ding J F, et al. Appl Microbiol Biotechnol, 2008, 81, 647-657.) used microbacterium oxydans to glycosylate puerarin, and obtained 7-O-glucoside puerarin (CASRN: 1163249-06-6) and 7-O-isomaltoside puerarin (CASRN: 1163249-07-7). The catalytic reaction took place with 4 g/L puerarin, 50 g/L cane sugar as glycosyl donor, at 30° C. for 48 h, the 7-O-glucoside puerarin mole conversion rate was 40%, and 7-O-isomaltoside puerarin mole conversion rate was 5%. Both converted products were separated and purified by a preparative HPLC method, and their water solubility was increased by respectively 18 times and 100 times as compared with puerarin. Huang et al (Huang W, Ochiai H, Zhang X Y, et al. Carbohyd Res, 2008, 343, 2903-2913.) used a acetyl galactosidase to convert puerarin by glycosylation in 20% DMSO with trimannose acetamido glucose oxazoline as glycosyl donor, and obtained the corresponding glycosidated compound Puerarin-GlcNAcMan3 (CASRN: 1093135-90-0). The catalytic reaction was conducted with 4.16 g/L puerarin and 13 g/L trimannose acetamido glucose oxazoline as a glycosyl donor, for 2 h at 23° C., Puerarin-GlcNAcMan3 mole conversion rate was 60%, but the preparation and relevant properties of this glycosylated product were not reported. Choi et al (Choi C H, Kim S H, Jang J H, et al. J Sci Food Agric, 2010, 90:1179-1184.) used malto-amylase (BSMA) glycosylated puerarin originating from fat bacillus thermophilus, and respectively obtained glucosyl-α-(1,6)-puerarin, maltosyl-α-(1,6)-puerarin and glucosyl-α-(1,3)-puerarin (CASRN: 1219937-73-1), with total yield rate of products of 56.7% at 10 g/L puerarin. Yu et al (Yu C G, Xu H D, Huang G D, et al. Appl Microbiol Biotechnol, 2010, 86:863-870.) treated microbacterium oxydans with 40% ethanol, changed the cellular permeability, and microbacterium oxydans can convert 7-O-glucoside puerarin to 7-O-fructoside puerarin (CASRN: 1223091-93-7). Zhang Lianwen et al (China Invention Patent Application No.: 200910068855.7; Publication No.: CN 101575631A) glycosylated puerarin with galactose transferase, in the catalytic reaction, with 9.12 g/L puerarin, 4 g/L UDP-galactose as glycosyl donor, semi-emulsified glycosyl-α-(1,4)-puerarin (CASRN: 1196677-60-7) was obtained, and its solubility is 12 times that of puerarin.

After puerarin is glycosylated, its water solubility is substantially increased. The molecular structure changes due to glycosylation do not affect the potency of puerarin, thus providing a puerarin glycosylated compound which can be administered at high concentrations. The relevant reports are as follows: Chung et al (Chung M J, Sung N J, Park C S, et al. Eur J Pharmacol, 2008, 578, 159-170.) used the mixture of equimolar glucosyl-α-(1,6)-puerarin (CASRN: 824959-75-3) and maltosyl-α-(1,6)-puerarin (CASRN: 824959-76-4) as water soluble puerarin glycosylation product, and the pharmacological experiment in HepG2 cells and C57 BL/6J mice showed that: the water soluble puerarin glycosylation product maintained the same potency as puerarin to resist oxidation activity and lower LDL oxidation. The in vitro pharmacokinetic experiment conducted by Jiang Jierong et al (Jiang J R, Yuan S, Ding J F, et al. Appl Microbiol Biotechnol, 2008, 81, 647-657.) with 7-O-glucoside puerarin (CASRN: 1163249-06-6) showed that: as compared with puerarin, 7-O-glucoside puerarin demonstrated better pharmacokinetic performance, the plasma half-life (t1/2) and mean retaining time (MRT) of 7-O-glucoside puerarin were respectively 2 times and 2.8 times that of puerarin, and this performance could possibly increase the bio-availability of 7-O-glucoside puerarin. Yuan Sheng et al (China Invention Patent Application No.: 200710021700.9) prepared drug to treat and prevent cardio-cerebral vascular diseases with 7-O-glucoside puerarin or 7-O-isomaltoside puerarin and their drug combination. Zhang Lianwen et al (China Invention Patent Application No.: 200910068855.7; Publication No.: CN 101575631A) compared the vasodilatation effect of puerarin and semi-emulsified glycosyl-α-(1,4)-puerarin on vascular smooth muscle with the aorta vascular smooth muscle as the physiological model, and found that semi-emulsified glycosyl-α-(1,4)-puerarin could produce better vasodilatation effect than puerarin.

Due to relatively poor water solubility of puerarin, however, the above mentioned bioconversion method of puerarin glycosylation has limitations because the puerarin concentration is generally low before conversion (all below 10 g/L), and the mole conversion rate of products is also low (all below 70%). These restrictions have made it quite difficult to obtain a sufficient amount of products for pharmacological experiment on related cardio-cerebral vascular and tumor diseases and the subsequent commercial production.

SUMMARY OF THE INVENTION

For solving the above-mentioned problems, one object of this invention is to provide a new type of fructosyl puerarin.

Another object of this invention is to provide a preparation method of the described fructosyl puerarin. Specifically, this is a method of making fructosyl puerarin through aqueous phase or nonaqueous phase bioconversion by Arthrobacter nicotianae (Scientific name in Latin: Arthrobacter nicotianae XM6; classification nomenclature: Arthrobacter nicotianae XM6, deposited at China Typical Culture Collection Center on Jun. 29, 2010, address: Wuhan University, Wuhan, China, post code 430072, collection No.: CCTCC NO: M2010164).

A further object of this invention is to provide a use of the described fructosyl puerarin in preparing a medicament for treating cardio-cerebral vascular related diseases.

A still further object of this invention is to provide an application of the described fructosyl puerarin in preparing drugs to treat tumour related diseases.

These objects of the present invention are realized with the following technical solutions.

In one respect, this invention provides a fructosyl puerarin, the described fructosyl puerarin has the structure as shown in Formula (I) below:

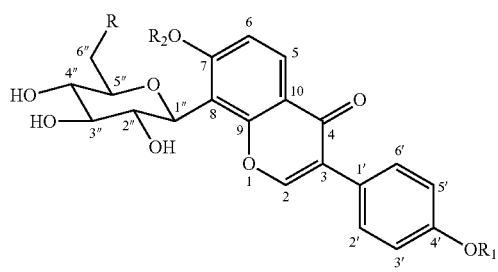

where, $R_1$ and $R_2$ are respectively and independently selected from hydrogen, methyl, ethyl, formoxyl, acetyl, methylamino and sulfonic acid; R is the oligosaccharyl connected by single glycosyl of fructose or 2 to 5 fructose molecules, with the structure as shown in Formula (II):

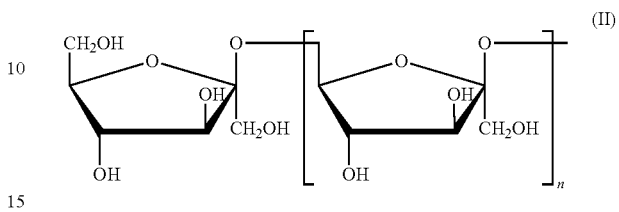

where n=0~4.

In another respect, this invention provides the method to prepare the above-mentioned fructosyl puerarin, the described method includes using fermentation liquor, fermentation liquor supernatant, purified fructosylated enzyme, or its recombined expressed protein with fructosylated enzyme activity, to perform bioconversion reaction on the converted liquid containing puerarin, to convert puerarin into fructosyl puerarin.

Preferably, the described method also involves removing impurities such as bacteria cell or bacteria protein from the converted liquid after completion of conversion, followed by rotary evaporation or freeze drying of the target fraction obtained with resin purification, to obtain fructosyl puerarin powder or crystal.

Preferably, the described fermentation liquor or fermentation liquor supernatant is obtained from microbial fermentation with fructosylated puerarin activity. Further preferably, the described microorganism is Arthmbacter nicotianae XM6 (CCTCC NO: M2010164).

Preferably, the fermentation medium used in microbial fermentation contains: cane sugar 5-80 g/L, peptone 5-50 g/L, $KH_2PO_4$ 0.4-4 g/L, $CaCl_2$ 0.5-5 g/L, $MnSO_4$ 0.1-2 g/L, with pH6-8; the fermentation conditions are optimized as: 25~40° C., oscillating in at 10~400 rpm in shake flask or agitating in fermentation tank with ventilation, the speed and ventilatory capacity are 1~6 vvm, 10~400 rpm, fermenting for 6-48 hours; further preferably, fermentation medium contains cane sugar 15 g/L, peptone 25 g/L, $KH_2PO_4$ 2 g/L, $CaCl_2$ 2 g/L, $MnSO_4$ 0.2 g/L, pH7.5; the fermentation conditions are further optimized as: 30° C., oscillating in shake flask at 240 rpm for 16 hours or agitating in fermentation tank with ventilation, the speed and ventilatory capacity are 4 vvm, 300 rpm, fermenting for 6 hours.

Preferably, the described bioconversion reaction is performed in an aqueous phase or nonaqueous phase.

The described aqueous phase conversion conditions include: oscillating at 10-400 rpm in shake flask or agitating in fermentation tank, puerarin concentration is over 0.1 g/L to saturation, the glycosyl donor being fructose or cane sugar or mixture of the two, puerarin and glycosyl donor are at molar ratio of 1:1~1:200, fermentation liquor or fermentation liquor supernatant (containing fructosylated enzyme 10-100 U/mL) accounting for 10%-50% of the reaction system is added, for reaction in any buffer solution with pH 4~8, at a conversion temperature of 25~40° C., for 6~96 hours; the preference conditions are: 10 g/L puerarin and 100 g/L cane sugar as glycosyl donor, 20% fermentation liquor supernatant (containing fructosylated enzyme 30 U/mL) is added into a 5 L fermentation tank with 1/15 mol/L phosphate buffer (pH6.86), for agitated conversion at 30° C. and 300 rpm for 12 hours.

The described nonaqueous phase conversion conditions include: oscillating at 10~400 rpm in shake flask or agitating in fermentation tank, one or a number of 5~50% hydrophily organic solvents chosen from DMSO, DMF, acetonitril, methanol and acetone or ethanol, puerarin concentration at 5~200 g/L, preferable puerarin concentration at 5~120 g/L, glycosyl donor being fructose or cane sugar or mixture of the two, puerarin and glycosyl donor molar ratio as 1:1~1:200, 10%-50% fermentation liquor or fermentation liquor supernatant (containing frustocosylase 10-100 U/mL) is added, for reaction in any buffer solution with pH 4~8, at a conversion temperature of 25~40° C., for 6~96 hours; the preference conditions are: taking 20% DMSO, 107.5 g/L puerarin and 350 g/L cane sugar as glycosyl donor, 20% fermentation liquor supernatant (containing fructosylated enzyme 30 U/mL) is added into a 5 L fermentation tank with 1/15 mol/L phosphate buffer (pH6.86), for agitated conversion at 30° C. and 300 rpm for 72 hours.

Preferably, the described resin purification is to absorb converted liquid containing fructosylated puerarin with AB-8 macroporous resin. In case of nonaqueous phase conversion, the adsorption is preferably conducted after the organic solvent in converted liquid has been removed by low temperature evaporation or the organic solvent has been diluted to below a volumetric ratio of 2%. After adsorption, residual glycosyl donor is first removed with aneluent, and then the obtained fructosylated puerarin is eluted by gradient or phase with aneluent. Further preferably, residual glycosyl donor is eluted with distilled water at pH 4~4.5 at 10 times the bed column volume, and then gradient or phase elution is performed with 5~30% methanol or ethanol solution to respectively obtain fructosylated puerarin.

Preferably, the described method also involves eluting and recovering residual puerarin with theeluent. Further preferably, 100% methanol or ethanol is used to elute and recover residual puerarin.

Preferably, the described fructosylated enzyme or its recombined expressed protein is β-D-furan fructosidase or its recombined expressed protein.

Further preferably, the described β-D-furan fructosidase is originated from Arthrobacter bacteria, with molecular weight of about 60 kDa, and the first 5 amino acid sequence at N end is respectively ATEPV.

In another respect, this invention also provides a use of fructosylated puerarin in preparing drugs to treat cardio-cerebral vascular related diseases.

In one further respect, this invention also provides a use of fructosylated puerarin in preparing drugs to treat tumour related diseases.

Preferably, the described drug is an injection or an oral administration preparation.

The following is a detailed description of this invention:

To fulfill the purpose of this invention, this application adopts the following technical plan:

According to an embodiment of this invention, this invention provides a new type fructosylated puerarin as shown in Formula (I):

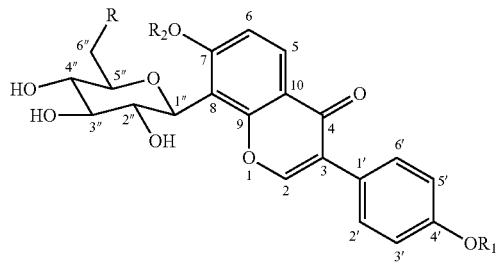

where, $R_1$ and $R_2$ is elected from the group consisting of the hydrogen group, methyl, ethyl, formoxyl, acetyl, methylamino and sulfonic acid.

In Formula (I), R is as shown in Formula (II):

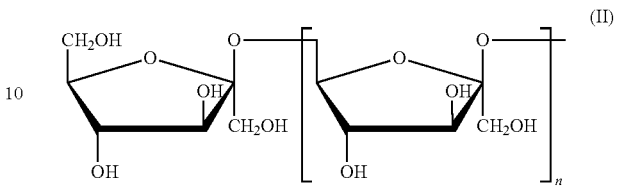

where n=0~4. R is the oligosaccharyl connected by single glycosyl of fructose or 2 to 5 fructose molecules.

This compound is prepared by an enzyme method, and can be purified with various conventional methods, such as chromatographic separation, liquid phase extraction and recrystallization method. The structure of this compound can be expressed by means of element analysis, infrared spectrum, visible and ultraviolet spectrum, NMR spectrum and monocrystal X-ray diffraction.

According to another embodiment of this invention, this invention provides a method to biologically convert fructosylated puerarin.

This invention uses the fermentation liquor, or fermentation liquor supernatant (exoenzyme), or the recombined expressed protein of this enzyme with fructosylated enzyme activity of puerarin, and it is added into the aqueous phase or nonaqueous phase converted liquid containing puerarin, to convert puerarin into fructosylated puerarin; after the end of conversion, the bacteria cell or bacteria enzyme protein in converted liquid is removed by heating, sedimentation and centrifugal separation, then the converted liquid is separated with AB-8 macroporous resin, while the target fraction is rotary evaporated or freeze dried to obtain fructosylated puerarin powder or crystal.

The above-mentioned microorganism strain with the puerarin fructosylation activity can be the microorganism or glycosidase of any fructosylated puerarin, especially Athrbacter nicotianae XM6 (CCTCC NO: M2010164).

The above-mentioned exoenzyme, or recombined expressed protein of that enzyme with puerarin fructosylation activity is the recombined expressed protein of β-D-furan fructosidase or β-D-furan fructosidase.

The above-mentioned β-D-furan fructosidase is produced from *Arthrobacter* bacteria.

There is no special restriction to the nutrient substance of the described culture medium, and it can be any nutrient medium suitable for growth of microorganisms, such as any culture medium with starch, glucose, corn starch and cane sugar as carbon source, with corn steep liquor and peanut meal as nitrogen source. The above-mentioned culture medium used for fermentation culture is: cane sugar 5-80 g/L, peptone 5-50 g/L, $KH_2PO_4$ 0.4-4 g/L, $CaCl_2$ 0.5-5 g/L, $MnSO_4$ 0.1-2 g/L, with pH 6-8.

The above-mentioned conditions for fermentation culture are: 25~40° C., oscillating at 10~400 rpm in shake flask or agitating in 5 L fermentation tank with ventilation, the speed and ventilatory capacity are 1~6 vvm, 10~400 rpm, and fermenting for 6-48 hours.

The above-mentioned bioconversion method and conversion reaction can be performed in either aqueous phase or nonaqueous phase. The conversion temperature range is 25~40° C., oscillating at 10~400 rpm in shake flask or agitating in 5 L fermentation tank with ventilation, for reaction of 6~96 h. (1) The aqueous phase conversion conditions are: puerarin concentration over 0.1 g/L to saturation, glycosyl donor as fructose or cane sugar or mixture of the two, puerarin to glycosyl donor molar ratio is 1:1~1:200, in any buffer solution with pH4~8; (2) nonaqueous phase conversion conditions are: using 5~50% hydrophily organic solvent DMSO, DMF, acetonitril, methanol, acetone and ethanol, puerarin concentration is 5~200 g/L, and preferably 5~120 g/L, glycosyl donor is fructose, cane sugar or mixture of the two, the puerarin to glycosyl donor molar ratio is 1:1~1:200, in any buffer solution with pH4~8;

The above-mentioned converted liquid containing fructosylated puerarin is adsorbed via AB-8 macroporous resin, and adsorption is conducted after the organic solvent in converted liquid has been removed by low temperature evaporation or the organic solvent has been diluted to below a volumetric ratio of 2%, in the first step, residual glycosyl donor is removed with distilled water at pH 4~4.5 (with pH adjusted by acetic acid) at 10 times the bed column volume as eluent. In the second step, the eluent is 5~30% methanol or ethanol solution for eluting by gradient or phase respectively to obtain fructosylated puerarin, and in the third step, the eluent is 100% methanol or ethanol for eluting off residual puerarin.

The above-mentioned fructosylated puerarin solution obtained via resin purification then undergoes rotary vaporization or freeze drying to obtain fructosylated puerarin powder or crystal.

In another embodiment of this invention, this invention provides an application of a new type puerarin glycosylated derivative in preparing drugs to treat cardio-cerebral vascular related diseases.

The monofructosyl-β(2,6)-puerarin of this invention can be used to prepare any drug of the pharmaceutically described form; in the described drug forms, injection or oral preparation will be preferred.

A test on the mice myocardial ischemia T wave amplitude variation with the compound of this invention monofructosyl-β(2,6)-puerarin shows that, with a dosage of respectively 12.5 mg/kg, 25 mg/kg and 50 mg/kg of the tested specimen monofructosyl-β(2,6)-puerarin, it can substantially reduce the T wave amplitude caused by pituitrin, and the amplitude of T wave reduction is less than that of puerarin, indicating that the tested specimen monofructosyl-β(2,6)-puerarin has better effect to resist myocardio ischemia than puerarin. The test result with the compound of this invention monofructosyl-β (2,6)-puerarin on myocardio ischemia mice heart rate shows that, 2 min. After injecting pituitrin, the heart rate of mice in all groups slowed down subsequently, and the heart rate starts to restore in all groups in 2~10 min. As compared with the control group, in groups with different dosage of the tested specimen monofructosyl-β(2,6)-puerarin, restoration of myocardio ischemia mice heart rate can be accelerated in all groups, and the restoration time of the group with low dosage of monofructosyl-β(2,6)-puerarin is shorter than that of the puerarin group. This indicates that the tested specimen monofructosyl-β(2,6)-puerarin has certain therapy effect on the heart disorder caused by myocardio ischemia. The fructosylated puerarin described in this invention can be prepared into a drug to treat cardio-cerebral vascular diseases.

According to one more embodiment of this invention, this invention provides the application of a new type puerarin glycosylated derivative in preparing drugs to treat tumour related diseases.

The monofructosyl-β(2,6)-puerarin of this invention can be used to prepare any drug of the pharmaceutically described form; in the described drug forms, injection or oral preparation will be preferred.

The test to suppress the in vitro proliferation of human breast cancer cell strain MDA-MB-231 and human chronmyelogenors leukemia cell strain K562 with the compound of this invention monofructosyl-β(2,6)-puerarin shows that: the monofructosyl-β(2,6)-puerarin can reduce the number of MDA-MB-231 cells after acting for 48 h. As compared with the control group during the same time period, there is difference when the dosage of monofructosyl-β(2,6)-puerarin reaches 50 µmol/L (P<0.05), substantial difference when the dosage reaches 100 µmol/L (P<0.01), and this difference becomes extremely apparent (P<0.001) when the dosage reaches 150 and 200 µmol/L, the suppression rate on MDA-MB-231 cells is respectively 44.04% and 59.42%, indicating that monofructosyl-p (2,6)-puerarin can markedly suppress proliferation of human breast cancer cell strain MDA-MB-231, and the suppression rate increases with the increase of dosage. The monofructosyl-β(2,6)-puerarin can reduce the number of K562 cells after acting for 48 h. As compared with the control group during the same time period, there is substantial difference with low dosage of monofructosyl-β(2,6)-puerarin at 1 µmol/L (P<0.05), and this difference becomes extremely apparent (P<0.001) when the dosage reaches 100, 150 and 200 µmol/L, the suppression rate of K562 cell is respectively 16.41%, 29.84% and 46.41%, indicating that monofructosyl-β(2,6)-puerarin can markedly suppress proliferation of human chronmyelogenors leukemia cell strain K562, and the suppression rate increases with the increase of dosage. This shows that the tested specimen monofructosyl-β(2,6)-puerarin has certain in vitro suppression effect on cancer cells.

The fructosylated puerarin described in this invention can be prepared into a drug to treat tumour diseases.

As compared with existing technologies, the beneficial results of this invention are:

First, the present invention provides a new fructosylated puerarin. Experiments have proved that this new type puerarin derivative has some therapy effect on heart disorders caused by myocardial ischemia and it can be effectively used to treat cardio-cerebral vascular diseases. Experiments have also proved that this new type puerarin derivative has significant in vitro suppression effect to the human breast cancer cell strain MDA-MB-231 and human chronmyelogenors leukemia cell strain K562, therefore it can be used to treat tumour diseases. These findings have expanded the source of puerarin glycosylated derivatives as drug, and no report has been seen in this aspect for existing puerarin glycosylated derivatives.

Secondly, as compared with puerarin, this new type fructosylated puerarin has better solubility and higher pharmacological activity, making up the defect of puerarin product, thus increasing the safety performance and therapy effect of the drug, making it a new drug product with good development prospects;

Furthermore, the inventor also provides the bioconversion method of this new type fructosylated puerarin. In glycosylation decoration of puerarin with existing bioconversion method, the puerarin concentration is generally low (all below 10 g/L) due to poor water solubility of puerarin, and the mole conversion rate of product is also low (all below 70%), with the bioconversion method of this invention, the obtained monofructosyl-β(2,6)-puerarin has a concentration as high as 111.7 g/L, with substrate conversion rate over 90%, this has solved the technical difficulties in the existing technologies and is conducive to pharmacological tests on cardio-cerebral vascular and tumour related diseases and subsequent industrial production of this product.

BRIEF DESCRIPTION OF THE DRAWING

In the following, the embodiments of this invention are described in detail in conjunction with attached figures, among them.

DETAILED DESCRIPTION OF PARTICULAR EMBODIMENTS OF THE INVENTION

Depository Information of Biological Material

Figure 1:
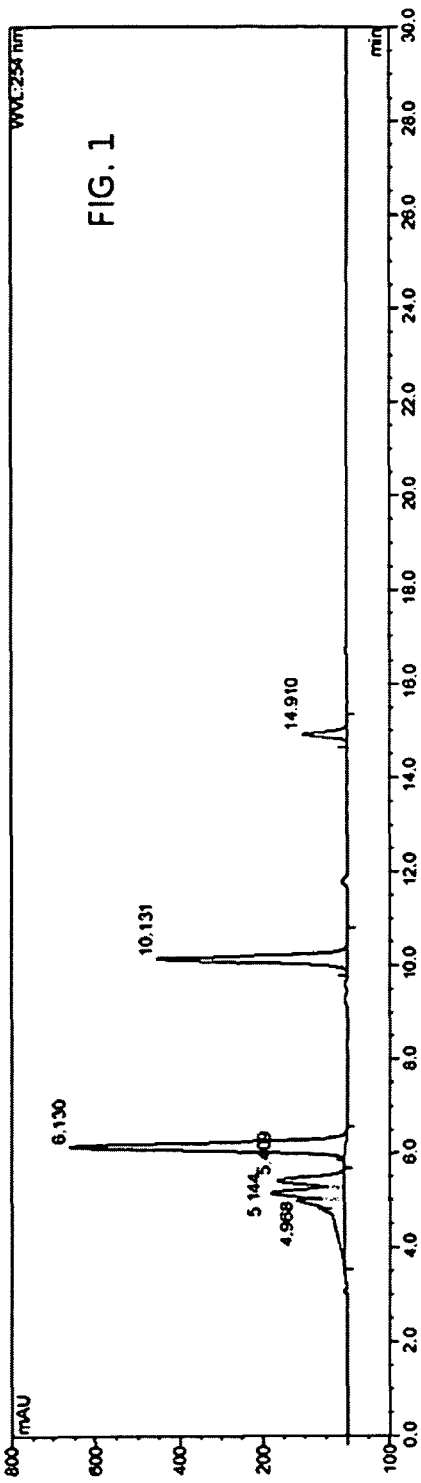
FIG. 1 shows the HPLC spectrum of aqueous phase bioconverted puerarin, in this figure: the peak with retention time of 14.910 mm is that of puerarin, the peak with retention time of 10.131 mm is that of monofructosyl-β(2,6)-puerarin, the peak with retention time of 6.130 min is that of bifructosyl-β(2,6)-puerarin, the peak with retention time of 5.409 min is that of trifructosyl-β(2,6)-puerarin, the peak with retention time of 5.144 min is that of tetrafructosyl-β(2,6)-puerarin, and the peak with retention time of 4.968 mm is that of pentafructosyl-β(2,6)-puerarin.

Scientific name in Latin: *Arthrobacter nicotianae* XM6, classification nomenclature: *Arthrobacter nicotianae* XM6, collected at China Typical Culture Collection Center on Jun. 29, 2010, address: Wuhan University, Wuhan China, Postal code: 430072, collection No.: CCTCC NO: M2010164.

Optimum Embodiment of Invention

The various features of novelty which characterize the invention are pointed out with particularity in the claims annexed to and forming a part of this disclosure. For a better understanding of the invention, its operating advantages, and specific objects attained by its use, reference should be made to the drawings and the following description in which there are illustrated and described preferred embodiments of the invention.

It can be understood that, the specific embodiments described herein are expressed by examples, which are not intended to restrict this invention. Without deviating from the scope of this invention, the main features of this invention can be applied in various embodiments. Technical personnel in this field will be aware or can confirm that, many equivalents can be applied in the specific steps described herein only by conventional experiments. These equivalents are regarded as being within the scope of this invention and be covered by the claims.

In the following embodiments, processes and methods not described in detail are generally known conventional methods in this field. The sources and trade names of the reagents used and their components necessarily to be listed are indicated in their first appearance, and they will be identical to those first indicated if there is no specific note for the same reagent used.

Embodiment 1: Obtaining Fructosylated Puerarin by Aqueous Phase Bioconversion of Puerarin Put 40 mL of fermentation cultured medium 2 (culture medium composition as shown in Table 1) into a 250 mL triangle flask, after sterilizing with 121° C. HP steam for 20 min, *Arthrobacter nicotianae* XM6 (CCTCCNO: M2010164) is inoculated, and at 30° C., the fermentation culture is oscillated at 180 rpm for 16 hours, before being inoculated as seed solution to a 5 L fermentation tank, at an amount of 5% of volume, the fermentation tank contains liquid of 3 L and has been sterilized in the same way as the shake flask. It is cultured by fermentation at 30° C. and 300 rpm, with ventilation flow of 3 vvm, for 6 hours (OD about 10), then it is centrifuged at 8000 rpm for 20 min, to collect supernatant enzyme liquid, and determine the supernatant enzyme liquid containing fructosylated enzyme 30 U/mL. The following method is used to determine the enzyme activity:

Preparation of substrate solution: dissolve 0.4 g puerarin and 10 g cane sugar sufficiently in 100 mL of 1/15 mol/L phosphate buffer (pH6.86). The reaction system: take 2 mL of 1/15 mol/L phosphate buffer (pH6.86) and add it into 18 mL substrate solution, put it in 30° C. for reaction for 10 min, then immediately take out 100 µL and add it into 900 µL of methanol to terminate the reaction, as a blank control. Concurrently, take separately 2 mL enzyme liquid and add it into 18 mL substrate solution, put it in 30° C. for reaction for 10 min, then immediately take out 100 µL and add it into 900 µL of methanol to terminate the reaction, as specimen. Then make determination with HPLC. The enzyme activity unit is defined as: the amount of enzyme required to convert 1 µmol of puerarin per min. at 30° C. is an activity unit (1 U is 1 µmol/min). Definition of specific activity (U/mL): the enzyme activity number (U) in unit volume (mL) of enzyme liquid.

Add 600 mL supernatant enzyme liquid into a 5 L fermentation tank containing a total volume of 1/15 mol/L phosphate buffer (pH6.86) containing 10 g/L puerarin (purchased from Nanjing Zelang Medical Technology Co., Ltd.) and 100 g/L cane sugar, for puerarin glycosylation reaction at 30° C. and 300 rpm, and after 12 hours, terminate the conversion reaction by heating it at 45° C. for 2 hours. The converted liquid is tested with HPLC and the conversion rate of fructosylated puerarin is 95%, refer to FIG. 1 for result.

The above-mentioned converted liquid containing fructosylated puerarin is adsorbed by AB-8 macroporous resin (chromatographic column 40×600 mm, at flow rate of 10 mL/min), then residual glycosyl donor is removed with distilled water at pH 4~4.5 with pH adjusted by glacial acetic acid) 10 times the column bed volume, followed by gradient elution with 5%-30% methanol solution, to respectively obtain fructosylated puerarin (purity>97%), and finally 100% methanol is used to wash off pigment and puerarin.

The fructosylated puerarin with a purity>97% respectively undergoes 45° C. rotary vaporization or freeze drying to obtain monofructosyl-β(2,6)-puerarin powder or crystal 7.9 g, bifructosyl-β(2,6)-puerarin powder or crystal 16.8 g, trifructosyl-β(2,6)-puerarin powder or crystal 3.3 g, tetrafructosyl-β(2,6)-puerarin powder or crystal 3.2 g, and pentafructosyl-β(2,6)-puerarin powder or crystal 2.2 g.

Determination at 25° C. shows that, the solubility of monofructosyl-β(2,6)-puerarin is 26.0 g/L, and that of bifructosyl-β(2,6)-puerarin is 280.8 g/L, respectively 5 times and 54 times the solubility of puerarin (5.2 g/L) under the same conditions.

Figure 3:
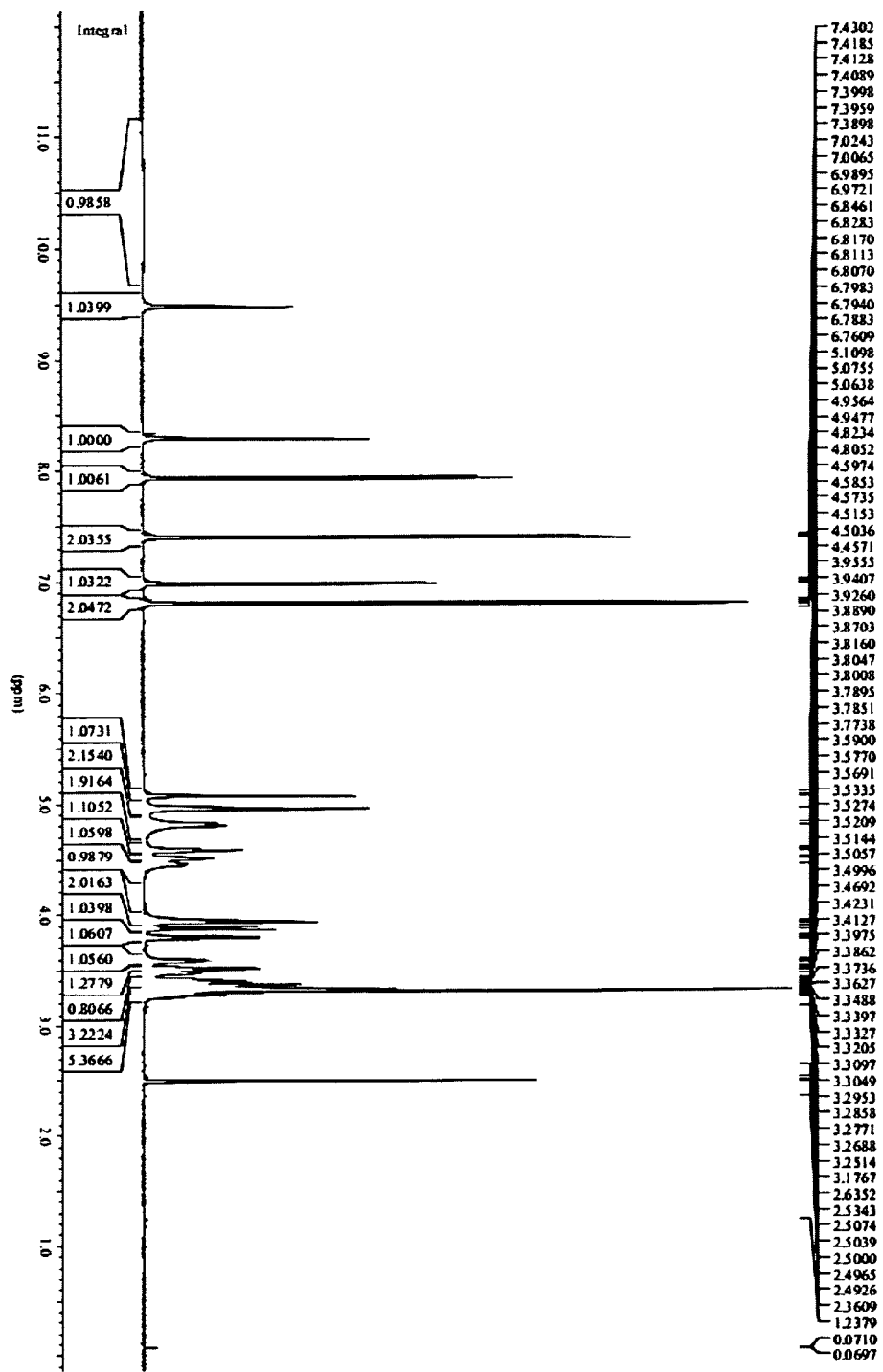
FIG. 3 shows the $^1$HNMR spectrum of monofructosyl-β(2,6)-puerarin.
Figure 4:
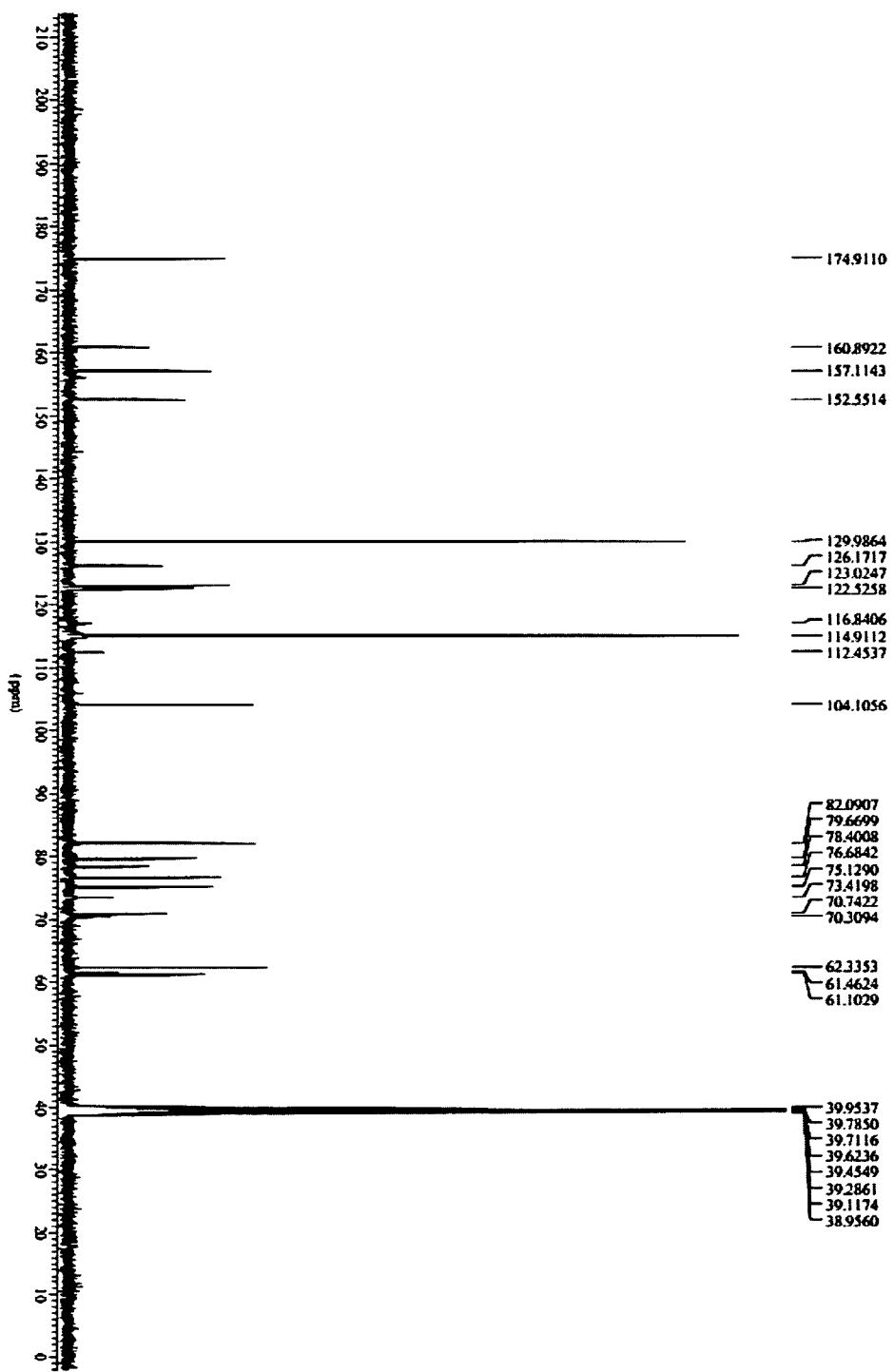
FIG. 4 shows the $^{13}$CNMR spectrum of monofructosyl-β(2,6)-puerarin.
Figure 5:
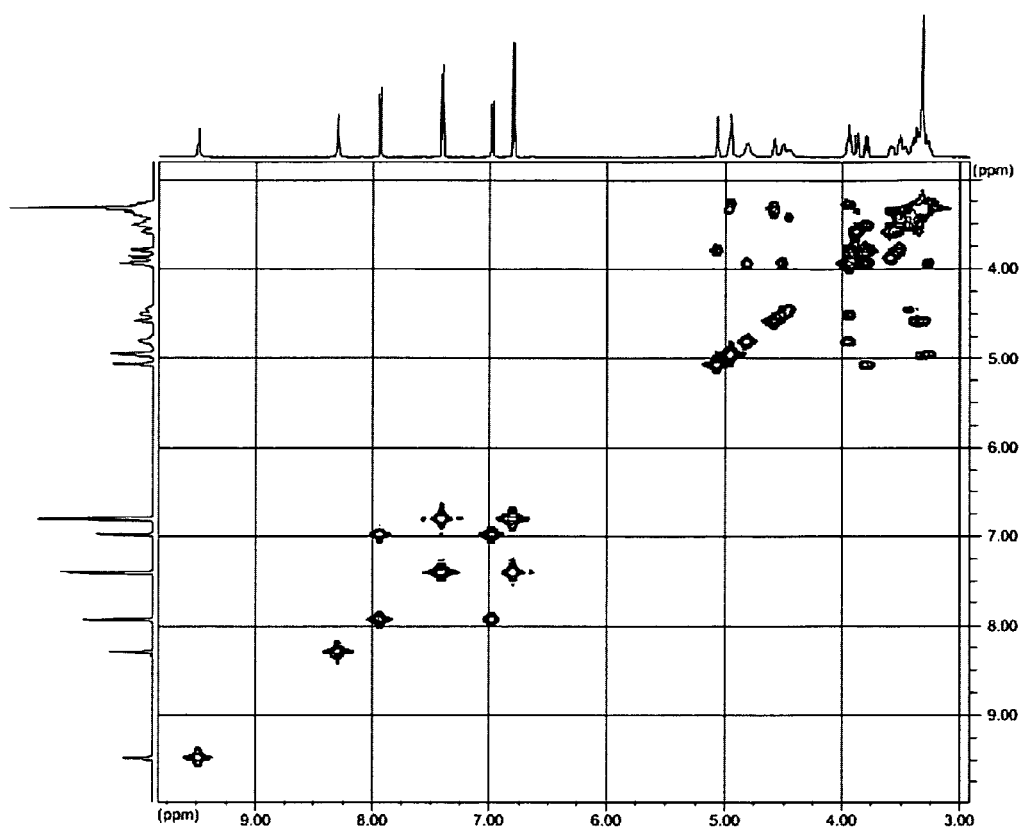
FIG. 5 shows the H—H COSY spectrum of monofructosyl-β(2,6)-puerarin.
Figure 6:
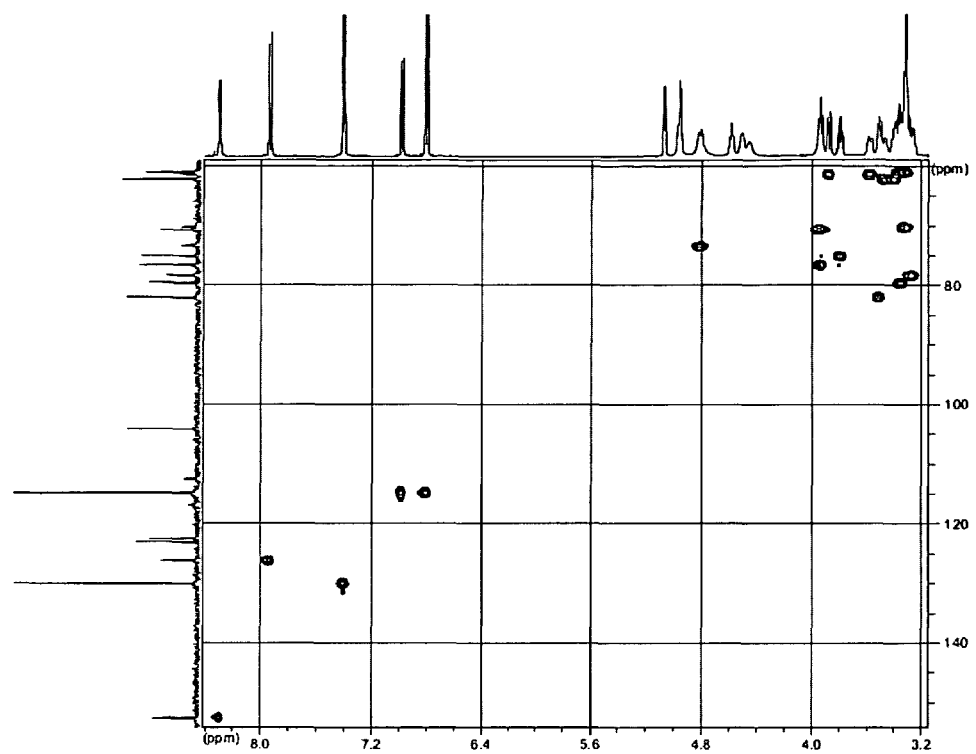
FIG. 6 shows the C—H HSQC spectrum of monofructosyl-β(2,6)-puerarin.
Figure 7:
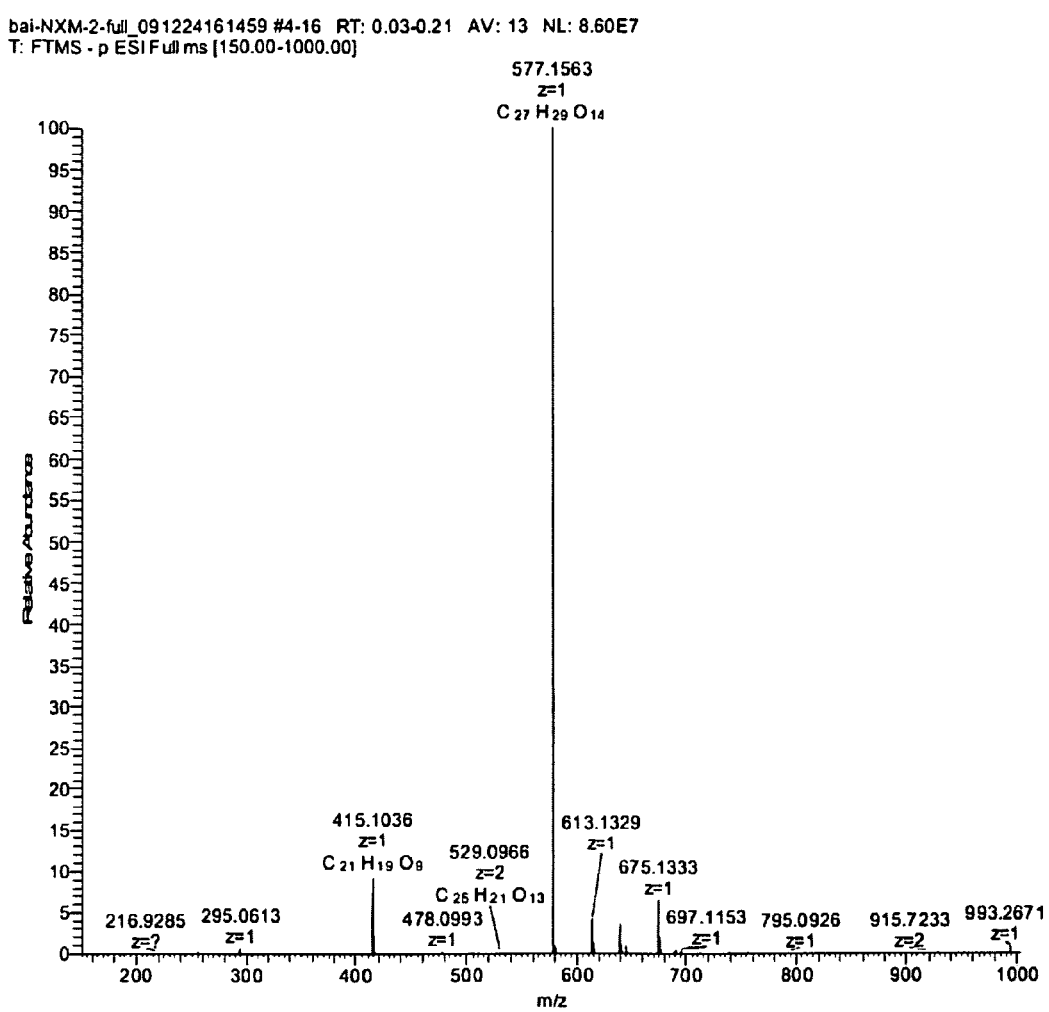
FIG. 7 shows the high resolution mass spectrum of monofructosyl-β(2,6)-puerarin.

The above-mentioned monofructosyl-β(2,6)-puerarin: HR-MS: m/z 577.1563[M−H]$^-$, with element composition $C_{27}H_{29}O_{14}$ (FIG. 7), and M-H calculated value 577.1557; at DMSO, the chemical displacement characteristics of $^1$H-NMR and $^{13}$C-NMR are respectively as follows:

$^1$H-NMR (500 MHz, DMSO-d$_6$) δ: 8.29(1H, s, H-2), 7.93 (1H, d, J=8.7 Hz, H-5), 6.98(1H, d, J=8.7 Hz, H-6), 7.40(2H, d, J=8.5 Hz, H-2'/H-6'), 6.80(2H, d, J=8.7 Hz, H-3'/H-5'), 9.48(1H, s, 4'-OH), 4.81(1H, d, J=9.1 Hz, H-1"), 3.93-3.96 (2H, m, H-2"/H-4'''), 3.79-3.89 (2H, m, H-5'''/H-6'''), 3.48-3.61 (3H, m, H-6", H-5''', H-6'''), 3.29-3.42 (6H, m, H-3", H-4", H-6", 2H-1''', H-3''') (FIG. 3, FIG. 5, FIG. 6) $^{13}$C-NMR (500 MHz, DMSO-d$_6$) δ: 174.9, 160.9, 157.1, 152.6, 130.0, 126.2, 123.0, 122.5, 114.9, 112.5, 116.8, 104.1(C-2'''), 82.1 (C-5'''), 79.7, 78.4, 76.7, 75.1(C-5"), 73.4, 70.7, 70.3, 62.3 (C-6"), 61.5(C-6'''), 61.1 (FIG. 4).

Figure 8:
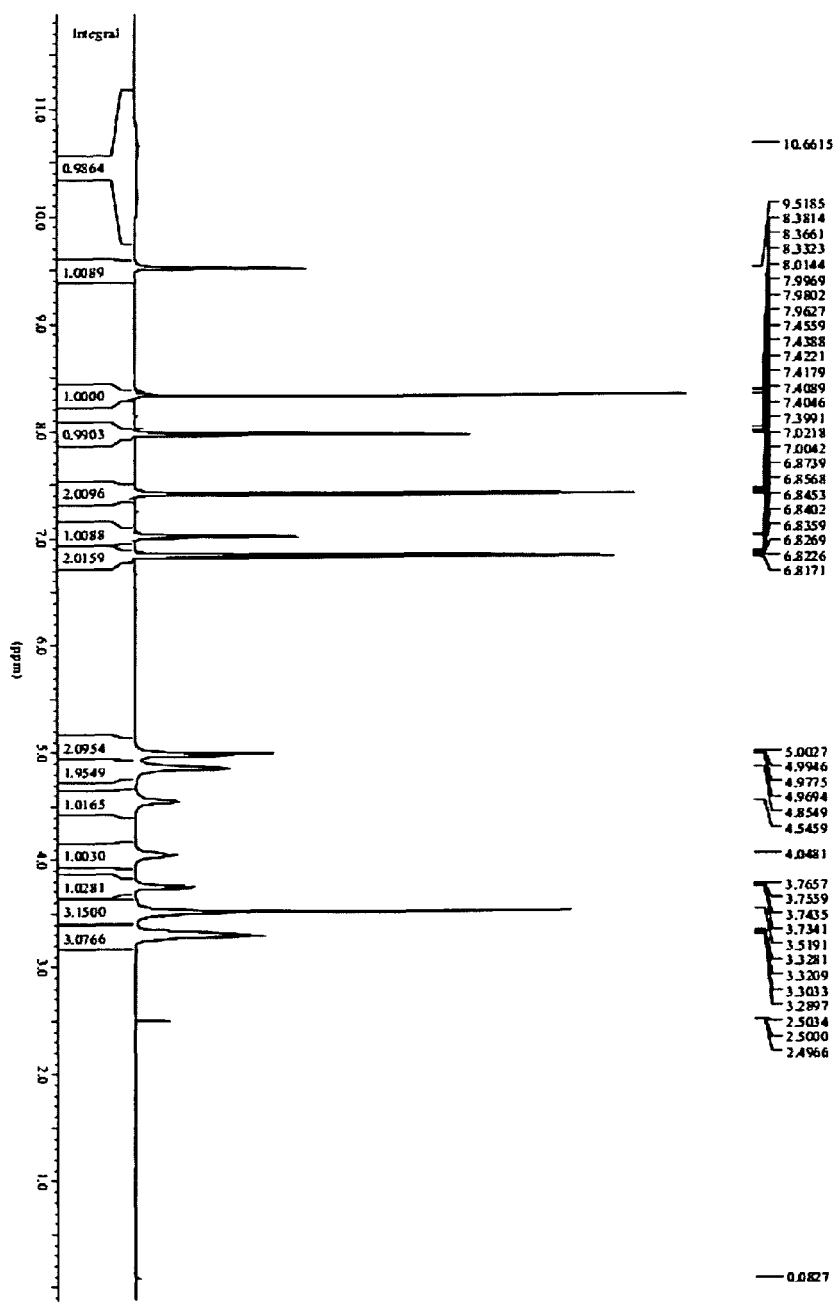
FIG. 8 shows the $^1$HNMR spectrum of puerarin.

The chemical displacement characteristics of puerarin $^1$NMR and $^{13}$C-NMR are respectively as follows:

$^1$H-NMR (500 MHz, DMSO-d$_6$) δ: 8.33(1H, s, H-2), 7.97 (1H, d, J=8.8 Hz, H-5), 7.01(1H, d, J=8.8 Hz, H-6), 7.41(2H, d, J=8.8 Hz, H-2'/H-6'), 6.83(2H, d, J=8.8 Hz, H-3'/H-5'), 9.52(1H, s, 4'-OH), 4.85(1H, d, J=9.0 Hz, H-1"), 4.05(1H, s, H-2"), 3.52, 3.75 (2H, m, 2H-6"), 3.26-3.36 (3H, m, H-3", H-4", H-5") (FIG. 8)

Figure 9:
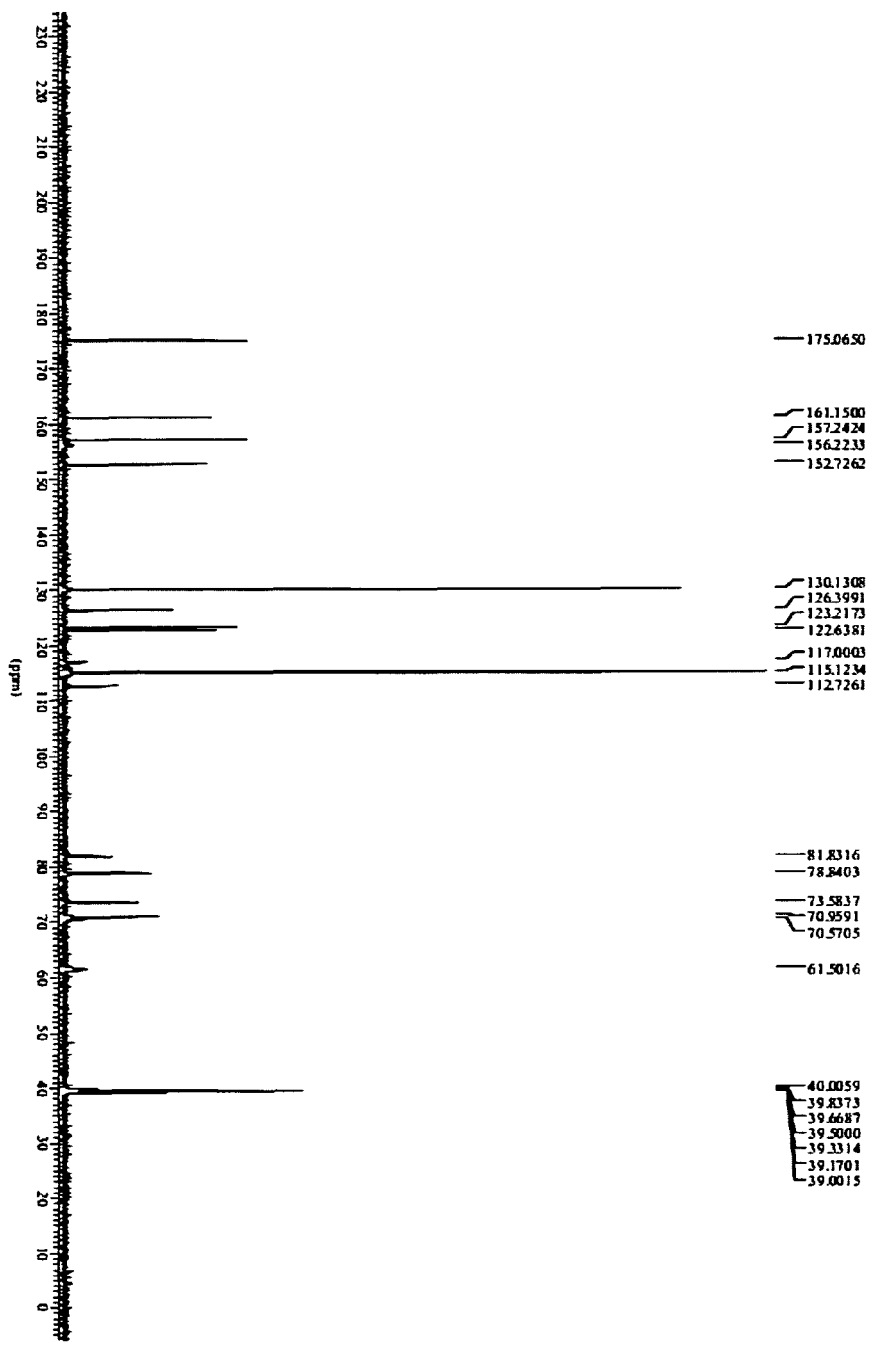
FIG. 9 shows the $^{13}$CNMR spectrum of puerarin.

$^{13}$C-NMR (500 MHz, DMSO-d$_6$) δ: 175.1, 161.2, 157.2, 152.7, 130.1, 126.4, 123.2, 122.6, 117.0, 115.19, 112.7, 81.8 (C-5"), 78.8, 73.6, 71.0, 70.6, 61.5(C-6") (FIG. 9).

Figure 10:
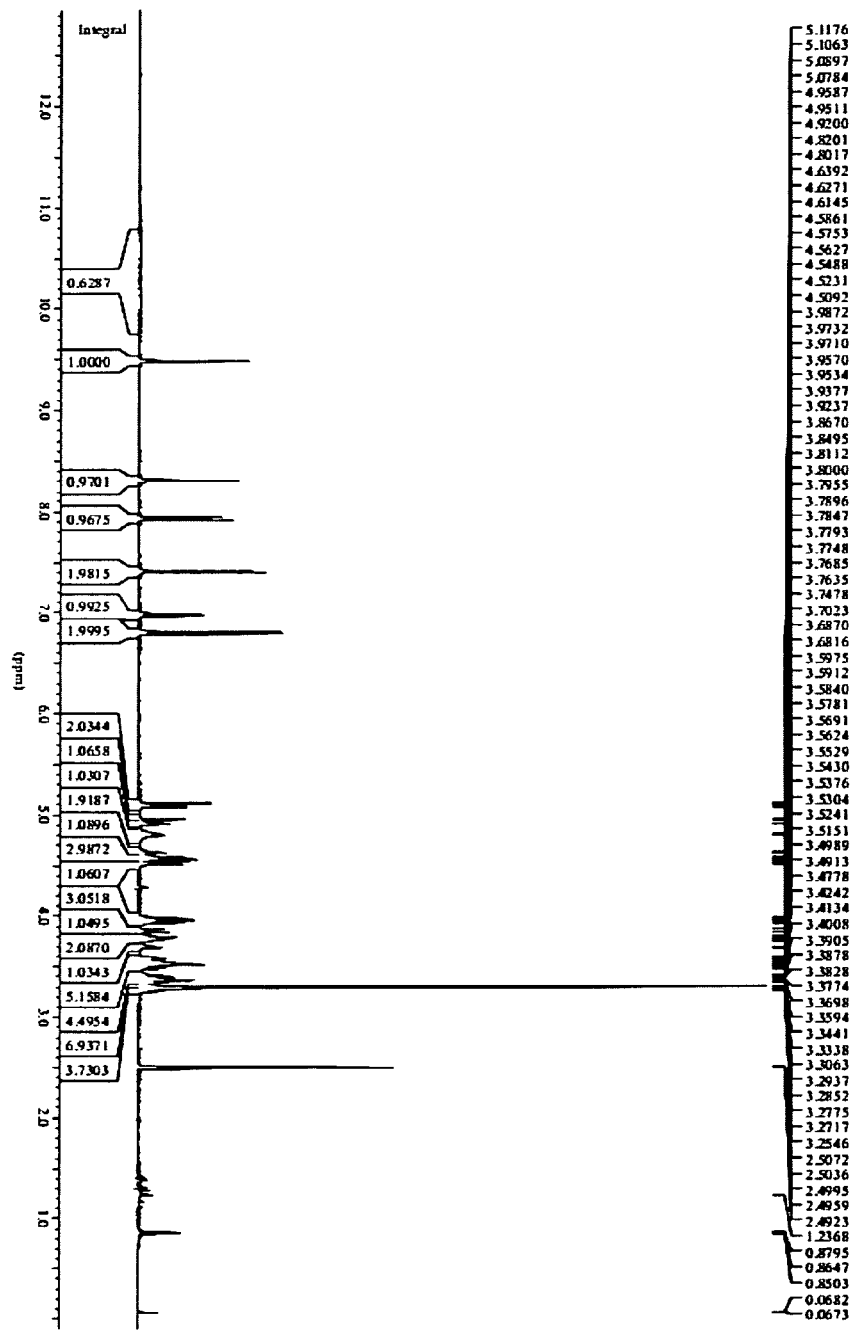
FIG. 10 shows the $^1$HNMR spectrum of bifructosyl-β(2,6)-puerarin.
Figure 12:
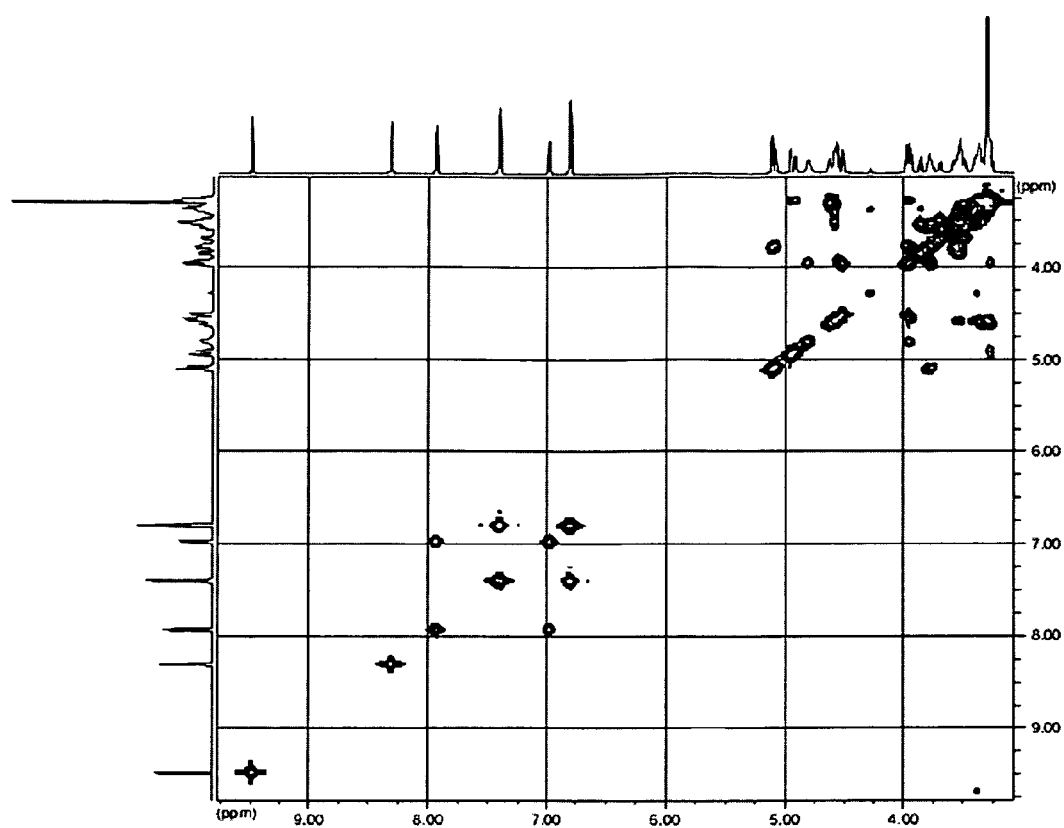
FIG. 12 shows the H—H COSY spectrum of bifructosyl-β(2,6)-puerarin.
Figure 13:
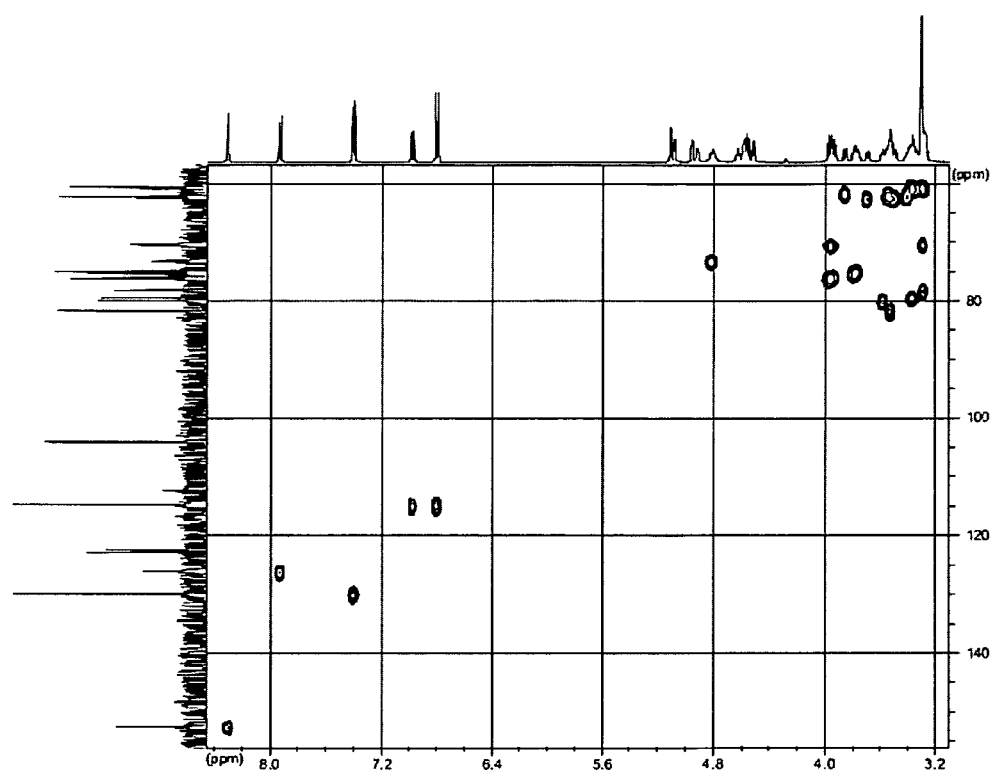
FIG. 13 shows the C—H HSQC spectrum of bifructosyl-β(2,6)-puerarin.
Figure 14:
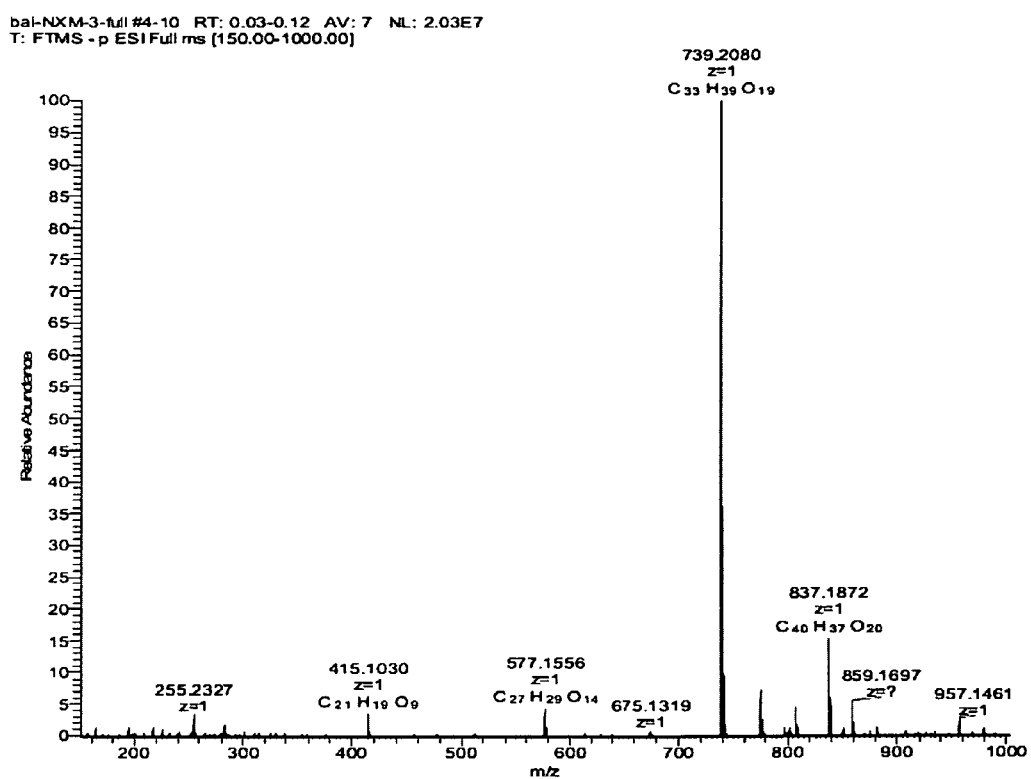
FIG. 14 shows the high resolution mass spectrum of bifructosyl-β(2,6)-puerarin.

Bifructosyl-β(2,6)-puerarin: HR-MS: m/z 739.2080[M−H]$^-$, with element composition $C_{33}H_{39}O_{19}$ (FIG. 14), M-H calculated value 739.2086; at DMSO, the chemical displacement characteristics of $^1$H-NMR and $^{13}$C-NMR are respectively as follows:

$^1$H-NMR (500 MHz, DMSO-d$_6$) δ: 8.29 (1H, s, H-2), 7.95 (1H, d, J=8.7 Hz, H-5), 6.97 (1H, d, J=8.8 Hz, H-6), 7.40 (2H, d, J=8.6 Hz, H-2'/H-6'), 6.80 (2H, d, J=8.8 Hz, H-3'/H-5'), 9.48 (1H, s, 4'-OH), 4.81(1H, d, J=9.2 Hz, H-1"), 3.92-3.99 (3H, m, H-2", H-4''', H-4''''), 3.69-3.87 (4H, m, H-6", H-5", H-5''', H-6''''), 3.48-3.58 (5H, m, H-6", H-3''', H-6''', H-5'''', H-6''''), 3.25-3.42 (8H, m, H-3", H-4", 2H-1''', H-6''', 2H-1'''', H-3'''') (FIG. 10, FIG. 12, FIG. 13).

Figure 11:
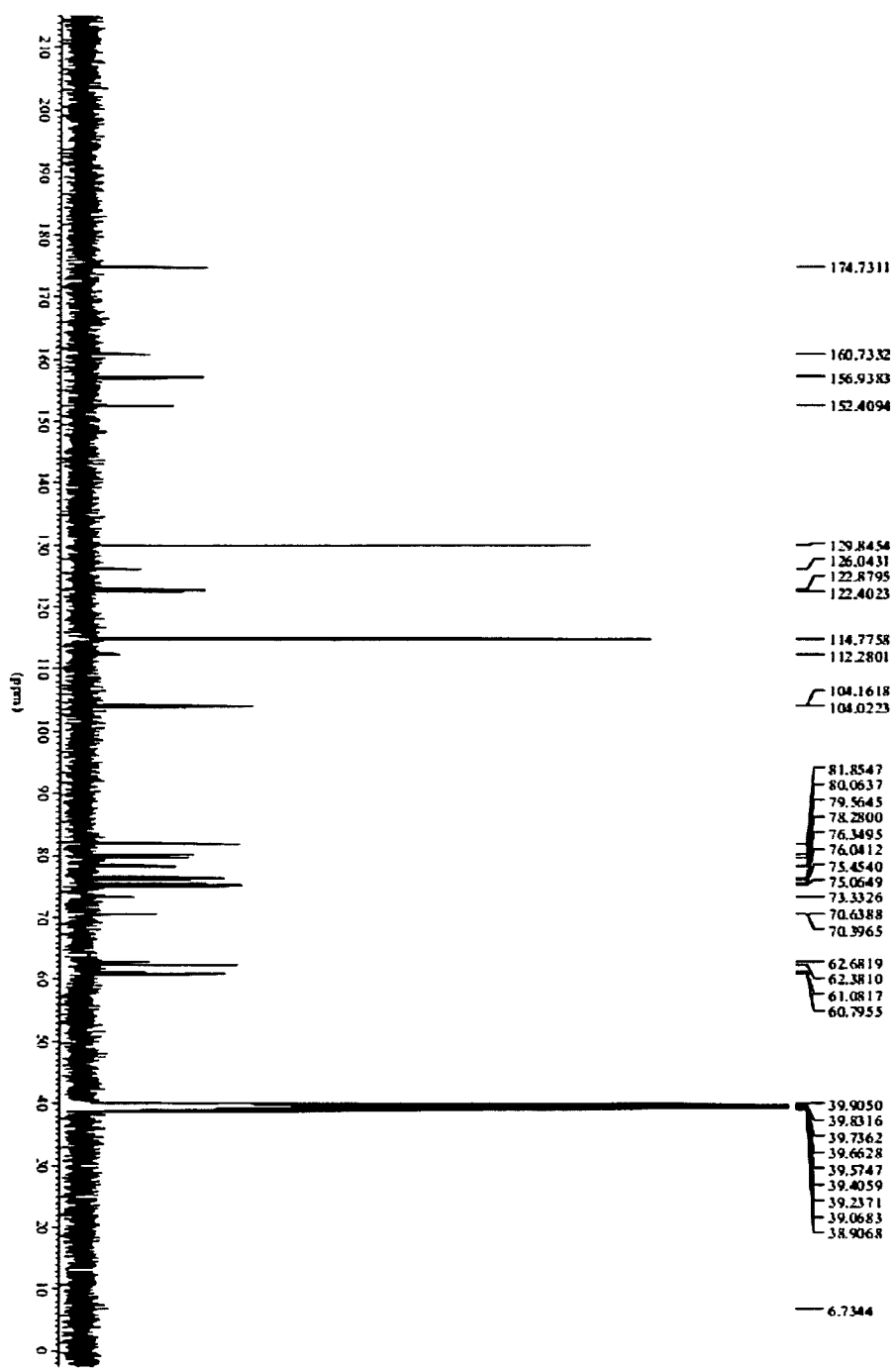
FIG. 11 shows the $^{13}$CNMR spectrum of bifructosyl-β(2,6)-puerarin.

$^{13}$C-NMR (500 MHz, DMSO-d$_6$) δ: 174.7, 160.7, 156.9, 152.4, 129.8, 126.0, 122.9, 122.4, 116.6, 114.8, 112.3, 104.2, 104.0, 81.9(C-5''''), 80.1, 79.6, 78.3, 76.3, 76.0, 75.5(C-5'''), 75.1(C-5"), 73.3, 70.6, 70.4, 62.7(C-6"), 62.4(C-6'''), 62.0(C-6''''), 61.1, 60.8 (FIG. 11).

Figure 15:
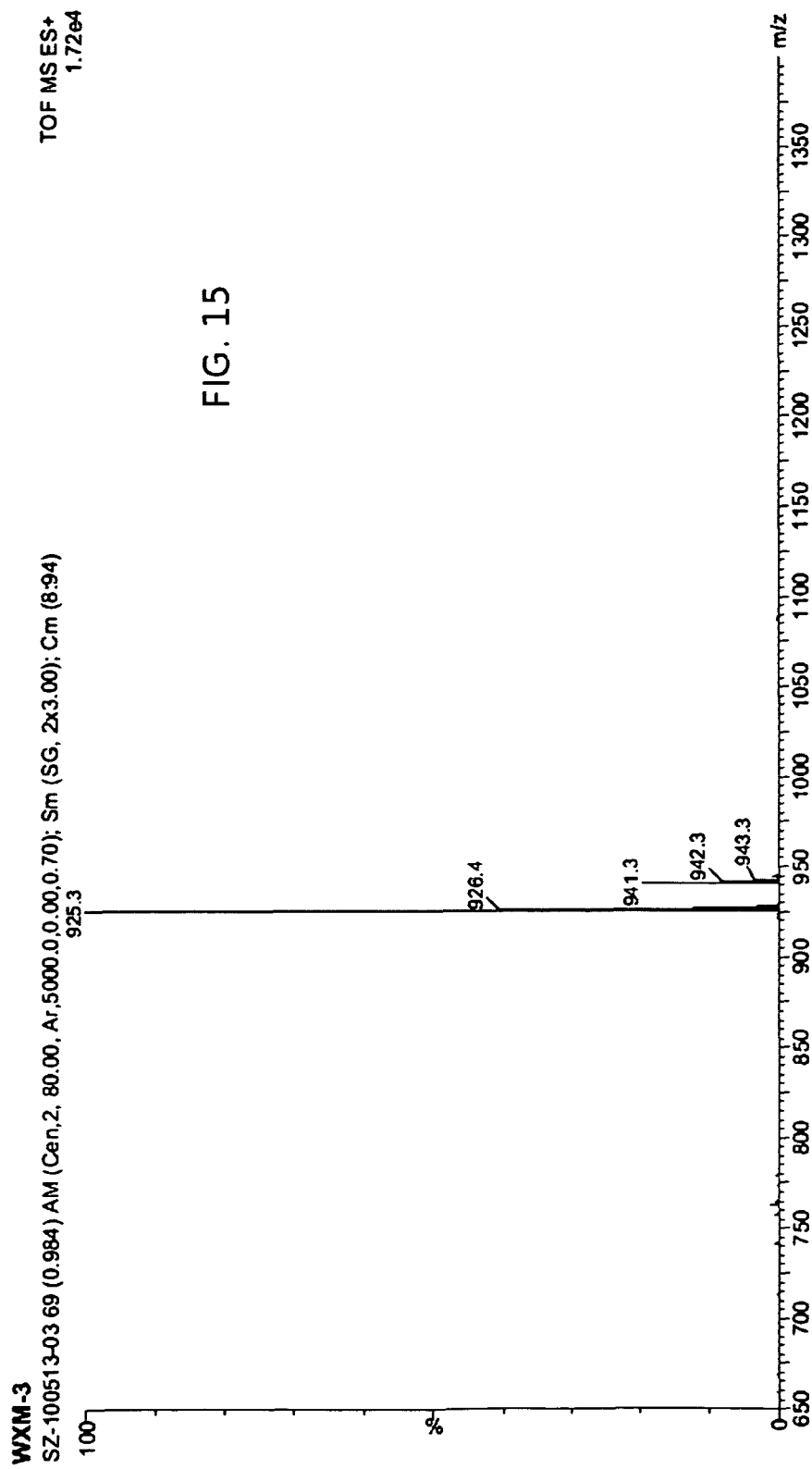
FIG. 15 shows the mass spectrum of trifructosyl-β(2,6)-puerarin.
Figure 16:
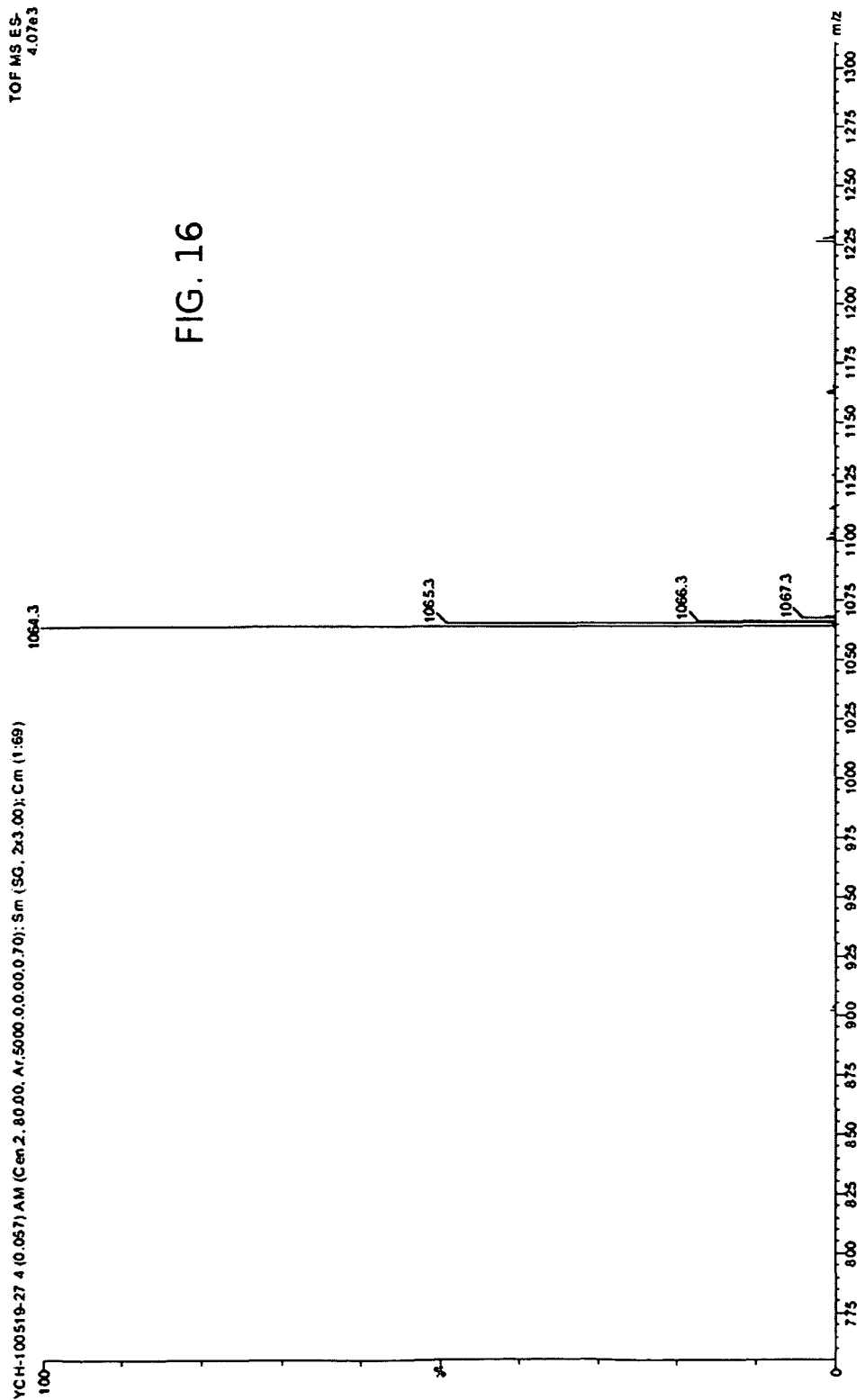
FIG. 16 shows the mass spectrum of tetrafructosyl-β(2,6)-puerarin.
Figure 17:
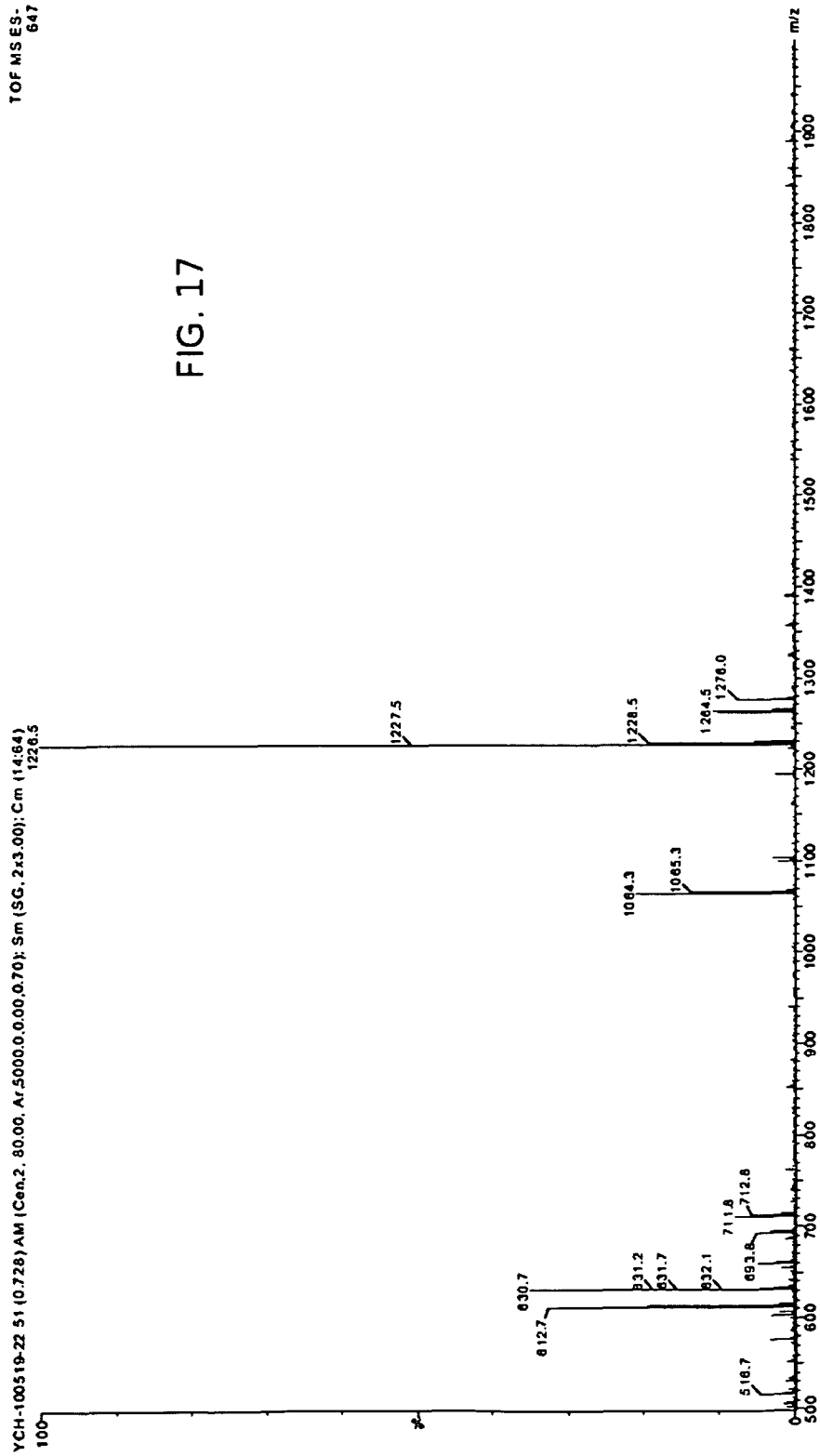
FIG. 17 shows the mass spectrum of pentafructosyl-β(2,6)-puerarin.

Trifructosyl-β(2,6)-puerarin: ESI-MS: m/z 925.3[M+Na]$^+$, with element composition $C_{39}H_{50}O_{24}Na$ (FIG. 15); tetrafructosyl-β(2,6)-puerarin: ESI-MS: m/z 1064.3[M−H]$^-$, with element composition $C_{45}H_{59}O_{29}$ (FIG. 16); pentafructosyl-β(2,6)-puerarin: ESI-MS: m/z 1226.5[M−H]$^-$, with element composition $C_{51}H_{69}O_{34}$ (FIG. 17).

Embodiment 2: Obtaining Fructosylated Puerarin by Non-aqueous Phase Bioconversion of Puerarin Put 40 mL of fermentation cultured medium 2 (culture medium composition as shown in Table 1) into a 250 mL triangle flask, after sterilizing with 121° C. HP steam for 20 min, Arthrobacter nicotianae XM6 (CCTCCNO: M2010164) is inoculated, and at 30° C., the fermentation culture is oscillated at 180 rpm for 16 hours, before being inoculated as seed solution to a 5 L fermentation tank, at an amount of 5%, the fermentation tank contains liquid of 3 L and has been sterilized in the same way as the shake flask. It is cultured by fermentation at 30° C. and 300 rpm, with ventilation flow of 3 vvm, for 6 hours (OD about 10), then it is centrifuged at 8000 rpm for 20 min, to collect supernatant enzyme liquid, and determine the supernatant enzyme liquid containing fructosylated enzyme 30 U/mL.

Figure 2:
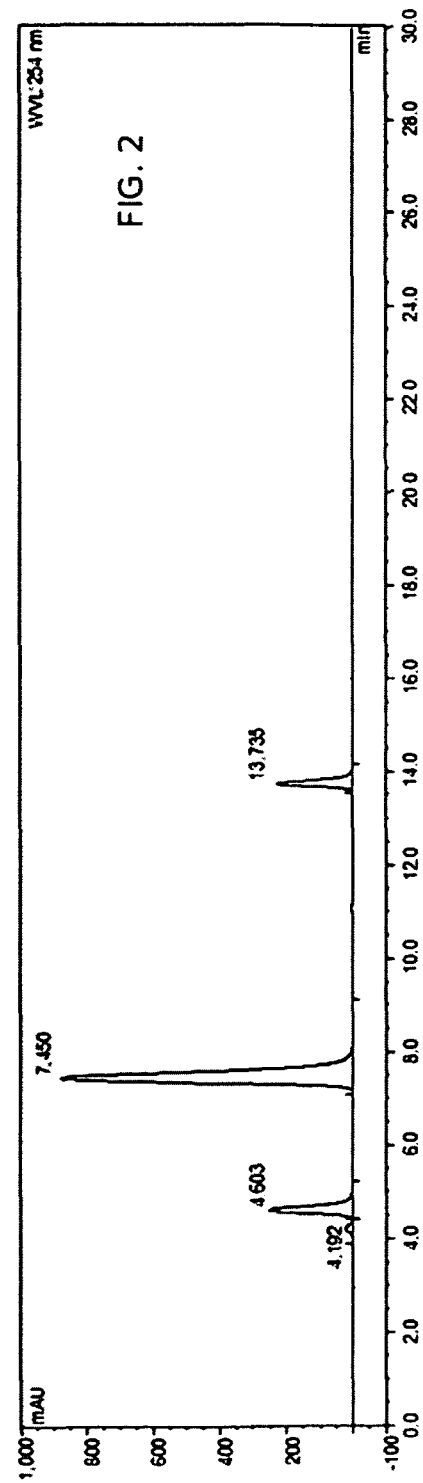
FIG. 2 shows the HPLC spectrum of nonaqueous phase bioconverted puerarin, in this figure: the peak with retention time of 13.735 min is that of puerarin; the peak with retention time of 7.450 mm is that of monofructosyl-β(2,6)-puerarin, the peak with retention time of 4.603 min is that of bifructosyl-β(2,6)-puerarin; and the peak with retention time of 4.192 min is that of trifructosyl-β(2,6)-puerarin.

Add 600 mL supernatant enzyme liquid into a 5 L fermentation tank with a total volume of 3000 mL of 1/15 mol/L phosphate buffer (pH 6.86) containing 107.5 g/L puerarin, 350 g/L cane sugar and 20% DMSO, for oscillated conversion at 30° C. and 300 rpm, and after 72 hours, terminate the conversion reaction by heating it at 45° C. for 2 hours. The converted liquid is tested with HPLC: monofructosyl-β(2,6)-puerarin reached 111.7 g/L, bifructosyl-β(2,6)-puerarin reached 28.3 g/L, trifructosyl-β(2,6)-puerarin reached 2.3 g/L, and the conversion rate of fructosylated puerarin derivative is 90%, refer to FIG. 2 for result.

The above-mentioned converted liquid containing fructosylated puerarin is diluted by 10 times and adsorbed by AB-8 macroporous resin (chromatographic column 40×600 mm, at flow rate of 10 mL/min), then residual glycosyl donor is removed with distilled water at pH 4~4.5 (with pH adjusted by glacial acetic acid) 10 times the column bed volume, followed by gradient elution with 5%-30% methanol solution, to respectively obtain fructosylated puerarin (purity>97%), and finally 100% methanol is used to wash off pigment and puerarin.

The fructosylated puerarin with a purity>97% respectively undergoes 45° C. rotary vaporization or freeze drying to obtain monofructosyl-β(2,6)-puerarin powder or crystal 270 g, bifructosyl-β(2,6)-puerarin powder or crystal 68 g, and trifructosyl-β(2,6)-puerarin powder or crystal 5 g.

Embodiment 3: Obtaining Fructosylated Puerarin by Non-aqueous Phase Bioconversion of Puerarin Put 40 mL of fermentation cultured medium 2 (culture medium composition as shown in Table 1) into a 250 mL triangle flask, after sterilizing with 121° C. HP steam for 20 min, Arthrobacter nicotianae XM6 (CCTCCNO: M2010164) is inoculated, and at 30° C., the fermentation culture is oscillated at 180 rpm for 16 hours (OD about 10), then it is centrifuged at 8000 rpm for 20 min, to collect supernatant enzyme liquid, which contains fructosylated enzyme 30 U/mL.

Add 4 mL supernatant enzyme liquid into a 250 mL triangle flask with plug with a total volume of 20 mL of phosphate buffer (pH6.86) containing 107.5 g/L puerarin, 350 g/L cane sugar and 20% DMSO, for oscillated conversion at 30° C. and 180 rpm, and after 72 hours, terminate the conversion reaction by heating it at 45° C. for 2 hours. The converted liquid is tested with HPLC: monofructosyl-β(2,6)-puerarin reached 111.7 g/L, bifructosyl-β(2,6)-puerarin reached 28.3 g/L, and trifructosyl-β(2,6)-puerarin reached 2.3 g/L, and the conversion rate of fructosylated puerarin is 90%.

The above-mentioned converted liquid containing fructosylated puerarin is diluted by 10 times and adsorbed by AB-8 macroporous resin (chromatographic column 20×600 mm, at flow rate of 10 mL/min), then residual glycosyl donor is removed with distilled water at pH4~4.5 (with pH adjusted by glacial acetic acid) 10 times the column bed volume, followed by gradient elution with 5%-30% methanol solution, to respectively obtain fructosylated puerarin (purity>97%), and finally 100% methanol is used to wash off pigment and puerarin. The fructosylated puerarin with a purity>97% respectively undergoes 45° C. rotary vaporization or freeze drying to obtain monofructosyl-β(2,6)-puerarin powder or crystal 1.8 g, bifructosyl-β(2,6)-puerarin powder or crystal 0.5 g, and trifructosyl-β(2,6)-puerarin powder or crystal 0.03 g.

TABLE 1

Different proportions of culture medium components

| Culture medium composition | Cane sugar (g/L) | peptone (g/L) | $KH_2PO_4$ (g/L) | $CaCl_2$ (g/L) | $MnSO_4$ (g/L) | pH |
|---|---|---|---|---|---|---|
| 1 | 5 | 5 | 0.4 | 0.5 | 0.1 | 6 |
| 2 | 35 | 25 | 2 | 2 | 0.5 | 7 |
| 3 | 80 | 50 | 4 | 5 | 2 | 8 |
| 4 | 5 | 25 | 2 | 2 | 0.5 | 7 |
| 5 | 35 | 50 | 0.4 | 0.5 | 0.1 | 6 |
| 6 | 80 | 5 | 4 | 5 | 2 | 8 |

TABLE 2

Mole conversion rate of monofructosyl-β (2,6)-puerarin (P1) and bifructosyl-β (2,6)-puerarin (P2) under different conditions

| Ferm. time (h) | Ferm. temp. (° C.) | Medium comp. | Conv. time (h) | Conv. temp. (° C.) | Conv. scale (mL) | Substrate concentration (g/L) | Molar ratio of substrate and cane sugar | Solvent | Solvent prop. (%) | P1 (%) | P2 (%) |
|---|---|---|---|---|---|---|---|---|---|---|---|
| 6 | 25 | 1 | 6 | 25 | 20 | 2 | 1:1 | DMF | 10 | 65 | 10 |
| 12 | 30 | 2 | 48 | 30 | 300 | 20 | 1:5 | Methanol | 20 | 73 | 17 |
| 18 | 40 | 3 | 96 | 35 | 3000 | 120 | 1:10 | DMSO | 40 | 42 | 0 |
| 6 | 30 | 4 | 6 | 25 | 20 | 2 | 1:1 | Acetone | 50 | 0 | 0 |
| 12 | 25 | 5 | 96 | 30 | 3000 | 100 | 1:10 | DMSO | 20 | 72 | 18 |
| 48 | 40 | 6 | 48 | 40 | 500 | 20 | 1:5 | Acetonitril | 20 | 20 | 0 |
| 6 | 30 | 6 | 36 | 25 | 500 | 20 | 1:5 | Ethanol | 20 | 30 | 0 |
| 12 | 40 | 2 | 72 | 30 | 3000 | 120 | 1:10 | DMSO | 30 | 65 | 16 |
| 48 | 25 | 3 | 96 | 40 | 20 | 2 | 1:1 | Ethanol | 30 | 10 | 0 |
| 6 | 40 | 1 | 48 | 25 | 500 | 60 | 1:5 | DMSO | 30 | 67 | 17 |
| 12 | 30 | 5 | 18 | 30 | 20 | 2 | 1:1 | Acetone | 10 | 68 | 13 |
| 48 | 25 | 1 | 6 | 40 | 3000 | 20 | 1:10 | Acetonitril | 40 | 0 | 0 |
| 6 | 40 | 3 | 96 | 25 | 3000 | 20 | 1:10 | Methanol | 40 | 10 | 0 |
| 12 | 25 | 2 | 24 | 30 | 500 | 120 | 1:5 | DMSO | 50 | 5 | 0 |
| 48 | 30 | 1 | 48 | 40 | 20 | 2 | 1:1 | DMF | 40 | 0 | 0 |

Embodiment 4: Effect of Different Fermentation and Conversion Conditions on Forming Products Put 40 mL of fermentation cultured medium (culture medium composition as shown in Table 1) into a 250 mL triangle flask, after sterilizing with 121° C. HP steam for 20 min, Arthrobacter nicotianae XM6) (CCTCCNO: M2010164) is inoculated, and after oscillated fermentation and culture under different fermentation conditions (the fermentation conditions as shown in Table 2), it is centrifuged at 8000 rpm for 20 min, to collect supernatant enzyme liquid, which contains fructosylated enzyme 10-100 U/mL. Add 20% supernatant enzyme liquid into the conversion system, after oscillated conversion under different conversion conditions (conversion conditions as shown in Table 2), terminate the conversion reaction by heating at 45° C. for 2 hours, and the converted liquid is tested with HPLC.

Different strain fermentation conditions and conversion conditions have different effect on the formation of puerarin glycosylated products, Table 1 and Table 2 show the change in mole conversion rate of the main products monofructosylated puerarin and bifructosylated puerarin in puerarin glycosylation reaction under different conditions.

It can be seen from the results in Table 2 that, the advantages of nonaqueous phase conversion are that the puerarin concentration in the conversion system can be increased to 120 g/L, under the preferred nonaqueous phase conversion conditions, the conversion rate in nonaqueous phase can be 90%, and the concentration of converted products is markedly increased (with total converted products over 140 g/L at 107.5 g/L of puerarin), moreover, the converted products can be regulated and controlled by selecting solvents and their proportion. These advantages of nonaqueous phase conversion will be conducive to industrial production.

Embodiment 5: Metabokinetic Experiment of monofructosyl-β(2,6)-Puerarin in Blood 1. Instruments and Chromatographic Conditions In HPLC analysis, DIONEX was used, with chromatographic column as Discovery HS C18 (250×4.6 μm, 5 μm), feeding specimen volume 20 μL, column temperature 30° C., the detector was UVD170U, with detection wavelength of 254 nm, flowing phase: A, water, B, chromatographic class methanol, A:B=80:20, at flow rate of 1 mL/min.

2. Experimental Animal

Sprague-Dawley mice (SD mice), with weight of 180-220 g, male and female in half, provided by Medical Experiment Center of Nantong University, with production permit No.: SCXK (Su) 20080010.

3. Experimental Method 3.1 Sample Collection

SD mice were randomly divided into 2 groups of 5 each, fasting for 12 hours before experiment. Puerarin and monofructosyl-β(2,6)-puerarin were respectively dissolved in 20% 1,2-PG normal saline, and injected into mouse caudal vein at a dosage of 50 mg/kg. After injection, at t=0 min, 4 min, 7 min, 17 min, 40 min, 60 min, 120 min and 180 min, 0.5 mL of blood was taken from orbit and put into centrifugal tubes treated with liquaemin, then it was immediately separated by centrifuging at 3000 rpm for 15 min, to separate out plasma for analysis.

3.2 Treatment of Specimens

Plasma of 100 μL was precisely taken and put into test tube, and 400 μL of methanol sedimented protein was added, they were mixed on vortex mixer for 5 min, then centrifuged at 10000 rpm for 10 min, and the supernatant was used for HPLC analysis.

3.3 Data Analysis

The plasma concentration of the puerarin and monofructosyl-β(2,6)-puerarin specimens prepared as per 3.2 was obtained by calculation with external reference method. The data obtained were analyzed using pharmacokinetics statistic software.

4. Results

It can be seen from the main metabokinetic parameters of puerarin and monofructosyl-β(2,6)-puerarin (Table 3) that, the t1/2, MRT (0-t) and MRT (0-∞) values of monofructosyl-β(2,6)-puerarin are obviously higher than those of puerarin, indicating longer residence time of puerarin derivatives in blood than puerarin, therefore it can have longer acting time in the body. Also, the AUC (0-t) and ACU (0-∞) values of puerarin derivatives are obviously higher than those of puerarin, indicating higher bioavailability of puerarin derivatives than puerarin.

TABLE 3

Metabokinetic parameters of puerarin and monofructosyl-P (2,6)-puerarin in mice (n = 5)

| Parameter | Puerarin | Monofructosyl-β (2,6)-puerarin |
|---|---|---|
| t½ min | 17.029 ± 3.086 | 19.741 ± 2.34 |
| CL L/min/kg | 0.013 ± 0.003 | 0.009 ± 0.001 |
| Y L/kg | 0.303 ± 0.045 | 0.256 ± 0.032 |
| AUC (0-t) mg/Lxmin | 4096.192 ± 973.839 | 5523.446 ± 688.104 |
| lACU (0-∞) mg/Lxmin | 4131.694 ± 1018.104 | 5605.211 ± 723.966 |
| MRT (0-t) min | 19.681 ± 5.075 | 25.707 ± 2.324 |
| MRT (0-∞) min | 20.576 ± 5.979 | 27.453 ± 2.976 | t½ = half life of clearance
CL = whole body clearance
AUC = area under concentration-time curve
MRT = average residence time Embodiment 6: Experiment on Protection Effect of monofructosyl-β(2,6)-Puerarin Mice Acute Myocardial Ischemia 1. Experimental Materials Pituitrin injection was purchased from Nanjing Xinbai Pharmaceutical Co., Ltd., normal saline injection from Nanjing Xiaoying Pharmaceutical Co., Ltd., and DMSO, PG, and anhydrous ethanol were of chromatographic class. The puerarin was purchased from Nanjing Zelang Medical Technology Co., Ltd., and monofructosyl-β(2,6)-puerarin was prepared with the method in this invention, and tested with HPLC for a purity of over 99%.

2. Experimental Animal

Sprague-Dawleymice (SD mice), with weight of 180-220 g, male and female in half, provided by Medical Experiment Center of Nantong University, with production permit No.: SCXK(Su) 20080010.

3. Experimental Method

50 SD mice sensitive to pituitrin were fed for adaption for 3 days, and divided on a random basis into solvent group, puerarin group, and low, medium and high monofructosyl-β(2,6)-puerarin groups, with 10 in each group. Drugs were dissolved with 10% PG solution, the administration was 0.5 mL, PG normal saline solution was used for solvent group, puerarin PG normal saline solution for puerarin group, at a dosage of 50 mg/kg, monofructosyl-β(2,6)-puerarin groups were given PG normal saline solution, at dosage respectively 12.5 mg/kg, 25 mg/kg and 50mg/kg. 5 min after drug injection, mice of all groups were injected slowly into vein Pit 0.5 U/kg to reproduce acute myocardio ischemia model, the ECG changes of mice in all groups were observed at 15 s, 30 s, 1 min, 5 min and 10 min after Pit injection, and the heart rate and T-wave amplitude variations at these time points were calculated.

4. Statistic Method

The data were presented with, and tested with t. P<0.05 indicates substantial difference, P<0.01 indicates very substantial difference; and P<0.001 indicates extremely substantial difference.

5. Results 5.1 Effect of Puerarin Derivatives on Mice Myocardial Ischemia T Wave Amplitude Variation

TABLE 4

Effect of monofructosyl-β (2,6)-puerarin (P1) on T wave amplitude variation of myocardio ischemia mice (N = 10, $\bar{X}$ ± SD)

| Group | Dosage/ mg·kg$^{-1}$ | Normal | 15 s | 30 s | 1 min | 2 min | 5 min | 10 min |
|---|---|---|---|---|---|---|---|---|
| Solvent group | — | / | 0.119 ± 0.146 | 0.150 ± 0.092 | 0.207 ± 0.065 | 0.178 ± 0.053 | 0.111 ± 0.048 | 0.055 ± 0.029 |
| Puerarin | 50 | / | 0.082 ± 0.052 | 0.114 ± 0.096 | 0.118 ± 0.086* | 0.132 ± 0.096 | 0.118 ± 0.075 | 0.074 ± 0.061 |

TABLE 4-continued

Effect of monofructosyl-β (2,6)-puerarin (P1) on T wave amplitude variation of myocardio ischemia mice (N = 10, $\bar{X} \pm SD$)

| Group | Dosage/ mg·kg$^{-1}$ | T wave amplitude variation/mv | | | | | |
|---|---|---|---|---|---|---|---|
| | | Normal | 15 s | 30 s | 1 min | 2 min | 5 min | 10 min |
| P1 high dosage group | 50 | / | 0.092 ± 0.067 | 0.118 ± 0.087 | 0.109 ± 0.084* | 0.106 ± 0.091 | 0.080 ± 0.070 | 0.082 ± 0.058 |
| P1 medium dosage group | 25 | / | 0.053 ± 0.027 | 0.105 ± 0.076 | 0.116 ± 0.088* | 0.112 ± 0.087 | 0.067 ± 0.038 | 0.054 ± 0.038 |
| P1 low dosage group | 12.5 | / | 0.082 ± 0.060 | 0.097 ± 0.084 | 0.051 ± 0.034*** | 0.102 ± 0.071* | 0.069 ± 0.040 | 0.068 ± 0.038 |

Note:
Compared with solvent group, *P < 0.05, P < 0.01, *P < 0.001

Experimental results show that, tested specimen monofructosyl-β(2,6)-puerarin at a respectively dosage of 12.5 mg/kg, 25 mg/kg and 50 mg/kg can all substantially reduce the T wave amplitude initiated by pituitrin, with reduction amplitude of T less than that of puerarin, indicating the tested specimen monofructosyl-β(2,6)-puerarin can better resist myocardial ischemia than puerarin.

5.2 Effect of Puerarin Derivative on Mocardial Ichemia Mice Heart Rate.

TABLE 5

Effect of monofructosyl-β (2,6)-puerarin (P1) on myocardio ischemia mice heart rate (N = 10, $\bar{X} \pm SD$)

| Group | Dosage/ mg·kg$^{-1}$ | Heart rate/time·min$^{-1}$ | | | | | | | |
|---|---|---|---|---|---|---|---|---|---|
| | | Normal | 5 s | 10 s | 15 s | 30 s | 1 min | 2 min | 5 min | 10 min |
| Model group | — | 465 ± 67 | 474 ± 29 | 448 ± 46 | 443 ± 44 | 423 ± 42 | 384 ± 35** | 360 ± 32** | 345 ± 35*** | 399 ± 43* |
| Puerarin | 50 | 484 ± 33 | 512 ± 36 | 469 ± 32 | 437 ± 63 | 411 ± 69* | 379 ± 85* | 379 ± 72** | 384 ± 53*** | 434 ± 51* |
| P1 high dosage group | 50 | 483 ± 91 | 485 ± 95 | 423 ± 84 | 420 ± 76 | 378 ± 34* | 327 ± 89** | 339 ± 45** | 347 ± 55** | 435 ± 72 |
| P1 medium dosage group | 25 | 474 ± 68 | 476 ± 65 | 442 ± 81 | 405 ± 88 | 428 ± 65 | 403 ± 54* | 386 ± 41** | 375 ± 37** | 420 ± 43 |
| P1 low dosage group | 12.5 | 403 ± 54 | 433 ± 63 | 416 ± 79 | 411 ± 75 | 389 ± 72 | 347 ± 71 | 339 ± 57* | 349 ± 50 | 395 ± 45 |

Experimental results show that, within 2 min. after injecting pituitrin, the heart rate of mice in all groups slowed down subsequently, and the heart rate starts to restore in all groups in 2~10 min. As compared with the control group, in groups with different dosage of the tested specimen monofructosyl-β(2,6)-puerarin, restoration of myocardial ischemia mice heart rate can be accelerated in all groups, and the restoration time of the group with low dosage of monofructosyl-β(2,6)-puerarin is shorter than that of the puerarin group. This indicates that the tested specimen monofructosyl-β(2,6)-puerarin has certain therapy effect on the heart disorder caused by myocardial ischemia.

Embodiment 7: Experiment of Monofructosyl-β(2.6)-Puerarin on Suppression of Cancer Cell Proliferation 1. Cell Strains and Drugs The human breast cancer cell strain MDA-MB-231, purchased from Shanghai Fument Gene Biotechnology Co., Ltd.; human chronmyelogenors leukemia cell strain K562, purchased from the cell bank of Chinese Academy of Sciences Shanghai Cell Research Institute; puerarin, purchased from Nanjing Zelang Medical Technology Co., Ltd.; and monofructosyl-β(2,6)-puerarin was prepared with the method in this invention, tested with HPLC to have a purity over 99%.

2. Experiment Drugs and Preparation of Solution

Drug stock solution: take 8.32 mg of puerarin powder and dissolve it in 2 mL DMSO, to get a puerarin solution of 10 mmol/L; take 11.56 mg of monofructosyl-β(2,6)-puerarin powder and dissolve it in 2 mL DMSO, to get monofructosyl-β(2,6)-puerarin solution of 10 mmol/L; filter them with a 0.22 μm filter, separate them in 1000 μL/doff and store them at −20° C., also, high concentration DMSO was filtered with a 0.22 μm filter for use by the control group.

Cell culture solution: take 1 bag of RPM 1-1640 culture medium (powder) and dissolve it in 800 mL of triple distilled water, agitate it with a magnetic agitator for at least half an hour to complete dissolution, and add 2 g of NaHCO$_3$, after complete dissolution dilute it to a constant volume of 1 L. Filter it with a filtration membrane of 0.22 pm to remove bacteria, and add serum to have a end serum concentration of 10%, and store it at 4° C.

PBS phosphate buffer: dissolve in 800 mL of distilled water 8 g NaCl, 0.2 g KCl, 1.44 g Na$_2$PO$_4$ and 0.24 g KH$_2$PO$_4$, adjust the solution with HCl to a PH value of 7.4, and add water to a constant volume of 1 L, sterilize it with HP steam for 20 min and store it at low temperature.

MTT application liquid: weigh and take 500 mg of MTT powder and dissolve it in100 mL PBS, agitate to allow it to dissolve, filter it with a filtration membrane of 0.22 μm to remove bacteria, split it and store it at 4° C. by avoiding light.

Triple liquid: take SDS 25 g, isopropanol 12.5 mL and concentrated HCl 2.5 mL and add triple distilled water to a constant volume of 1L, and store it at low temperature.

3. Main Reagents and Instruments

HPLC instrument (DIONEX model: P600); ELISA instrument (Molecular Devices Model: spectra MAX 190/GEMINIXS); $CO_2$ incubator (Forma Company Model: 3111); low speed centrifuge (Thermostat Model: PICO-17); inverted microscope (Leica Company Model: DMIL); horizontal rockers (Nanjing University Instruments Company Model: TY-80S); fetal calf serum (Hyclone Company); calf serum (Gibaco BRL Company); RPMI1640 (US Gibco Company); Penicillin G Sodium Salt (AMRESCO Company); Streptomycin Sulfate (AMRESCO Company); Trypsin (AMRESCO Company); and MTT (AMRESCO Company).

4. Cell Culture

MDA-MB-231 cells were cultured in an incubator at 37° C. with 5% $CO_2$ saturated humidity in the RPMI-1640 complete culture medium containing inactivated fetal calf serum with volume fraction of 10%, 100 U penicillin and streptomycin.

K-562 cells were cultured in an incubator at 37° C. with 5% CO2 saturated humidity in the RPMI-1640 complete culture medium containing inactivated calf serum with volume fraction of 10%, 100 U penicillin and streptomycin.

5. Experimental Methods 5.1 MDA-MB-231 Cell Toxicity Test

Take MDA-MB-231 cells in logarithmic phase (primary culture bottle) and discard the culture solution. Wash it once with 10 mL PBS, after discarding PBS, add 3 mL of 0.25% trypsin-0.04% EDTA, and after digesting at 37° C. for 3 min, add to it 5 mL of complete culture medium for neutralization reaction, and after blowing and beating, transfer the cells into a 15 mL centrifuging tube, to centrifuge it at 1000 rpm for 3 min. Prepare the suspended solution of cells and adjust the cell concentration with appropriate amount of complete culture medium to $3 \times 10^4$/mL. Fed the cells into a tissue culture plate 96, with cell suspended liquid of 180 μL in each case, and put the culture plate into a cell incubator (37° C., 5% $CO_2$) for conventional culture. When cells grew to 50%-70%, add drug liquid of different concentration. Take 10 mmol/L of puerarin and monofructosyl-β(2,6)-puerarin stock liquid and dilute with PBS in gradient the liquid respectively to 1000, 500, 100, 50, 10, 5, 1 and 0.1 μmol/L, and add 20 μL of drug in each case, the end concentration of drug being respectively 100, 50, 10, 5, 1, 0.5, 0.1 and 0.01 μmol/L. For DMSO solvent control group, add 20 μL of PBS containing corresponding drug and for the blank group, add 20 μL of PBS. For each drug concentration, 6 complex cases were provided. Put back the culture plate into the cell incubator, after 48 h, add 20 μL MTT (5 mg/mL) solution and continue to incubate it in the incubator for 4 h, then remove the supernatant and dry it with tissue, add 200 μL DMSO into each case and vibrate it in the rocker without light for 15 min, to allow the crystal to fully dissolve. Determine the light absorption at 490 nm with a fully automatic ELISA instrument, and calculate the average suppression rate, suppression rate (%)=(control group $A_{490}$–test group $A_{490}$)/control group $A_{490}$), the experiment was repeated three times.

5.2 K562 Cell Toxicity Test

Take K-562 cells in logarithmic phase and adjust the concentration to $1 \times 10^5$/mL, inoculate it to a tissue culture plate 96, with cell suspended liquid of 90 μL in each case, the experiment groups were treated with different end concentration (1, 5, 10, 20, 50, 100, 150, 200 μmol/L) of puerarin and monofructosyl-β(2,6)-puerarin, and add drug of 10 uL in each case, For DMSO solvent control group, add 20 μL of PBS containing corresponding drug solvent, and for the blank group, add 20 μL of PBS. For each drug concentration, 6 complex cases were provided. Put back the culture plate into the cell incubator, after 48 h, add 20 μL MTT (5 mg/mL) solution and continue to incubate it in the incubator for 4 h, then each case was added with triple liquid 100 μL, put it overnight to allow the crystal to fully dissolve. Vibrate it with oscillator for 20 min and determine the light absorption at 490 nm with a fully automatic ELISA instrument, and calculate the average suppression rate, suppression rate (%)=(control group $A_{490}$–test group $A_{490}$)/control group $A_{490}$), the experiment was repeated three times.

6. Statistic Processing

Relevant analysis and Student t tests in Microsoft Excel 2003 were used, and data are presented in X±SD.

7. Experimental Results 7.1 Effect of Puerarin Derivatives on Proliferation of Human Breast Cancer Cell Strain MDA-MB-231

TABLE 6

Effect of puerarin and monofructosyl-β (2,6)-puerarin in different concentration on MDA-MB-231 cell proliferation after acting for 48 h

| | Puerarin | | Monofructosyl-β (2,6)-puerarin | |
|---|---|---|---|---|
| Group | OD value | Average suppression rate (%) | OD value | Average suppression rate (%) |
| Control group | 0.707 ± 0.036 | | 0.701 ± 0.086 | |
| 0.5 μmol/L group | 0.632 ± 0.056 | 10.68 | 0.676 ± 0.021 | 3.68 |
| 1 μmol/L group | 0.624 ± 0.053* | 11.67 | 0.666 ± 0.069 | 5.02 |
| 5 μmol/L group | 0.619 ± 0.090* | 12.43 | 0.677 ± 0.081 | 3.47 |
| 10 μmol/L group | 0.610 ± 0.039** | 13.77 | 0.672 ± 0.085 | 4.20 |
| 50 μmol/L group | 0.531 ± 0.066** | 24.92 | 0.560 ± 0.062* | 20.17 |
| 100 μmol/L group | 0.473 ± 0.034*** | 33.06 | 0.500 ± 0.068** | 28.70 |
| 150 μmol/L group | 0.372 ± 0.037*** | 47.47 | 0.392 ± 0.041*** | 44.04 |
| 200 μmol/L group | 0.619 ± 0.042*** | 61.91 | 0.285 ± 0.067*** | 59.42 |

Note:
Compared with control group,
*P < 0.05,
**P < 0.01,
***P < 0.001.

The statistic results after analysis with MTT method show that (see Table 6), both puerarin and monofructosyl-β(2,6)-puerarin can reduce the number of MDA-MB-231 cells after acting for 48 h. As compared with the control group during the same time period, there is difference when the dosage of monofructosyl-β(2,6)-puerarin reaches 50 μmol/L (P<0.05), substantial difference when the dosage reaches 100 μmol/L (P<0.01), and this difference becomes extremely apparent (P<0.001) when the dosage reaches 150 and 200 μmol/L, the suppression rate on MDA-MB-231 cells is respectively 44.04% and 59.42%, indicating that monofructosyl-β(2,6)-puerarin can markedly suppress proliferation of human breast cancer cell strain MDA-MB-231, and the suppression rate increases with the increase of dosage.

7.2 Effect of Puerarin Derivative on Proliferation of Human Chronmyelogenors Leukemia Cell Strain K562.

TABLE 7

Effect of puerarin and monofructosyl-β (2,6)-puerarin in different concentration on K562 cell proliferation after acting for 48 h

| Group | Puerarin | | Monofructosyl-β (2,6)-puerarin | |
|---|---|---|---|---|
| | OD value | Average suppression rate (%) | OD value | Average suppression rate (%) |
| Control group | 1.026 ± 0.032 | | 1.027 ± 0.007 | |
| 1 μmol/L group | 0.917 ± 0.031*** | 10.65 | 0.950 ± 0.041** | 7.85 |
| 5 μmol/L group | 0.949 ± 0.023*** | 7.52 | 0.950 ± 0.018*** | 7.53 |
| 10 μmol/L group | 0.929 ± 0.030*** | 9.46 | 0.958 ± 0.022*** | 6.76 |
| 20 μmol/L group | 0.916 ± 0.056** | 10.68 | 0.963 ± 0.055* | 6.16 |
| 50 μmol/L group | 0.793 ± 0.083*** | 22.73 | 0.913 ± 0.048*** | 11.14 |
| 100 μmol/L group | 0.709 ± 0.038*** | 30.89 | 0.858 ± 0.028*** | 16.41 |
| 150 μmol/L group | 0.650 ± 0.039*** | 36.65 | 0.720 ± 0.055*** | 29.84 |
| 200 μmol/L group | 0.470 ± 0.027*** | 54.19 | 0.550 ± 0.086*** | 46.41 |

Note:
Compared with control group,
*P < 0.05,
**P < 0.01,
***P < 0.001.

The statistic results after analysis with MTT method show that (see Table 7), both puerarin and monofructosyl-β(2,6)-puerarin can reduce the number of K562 cells after acting for 48 h. As compared with the control group during the same time period, there is substantial difference with low dosage of monofructosyl-β(2,6)-puerarin at 1 μmol/L (P<0.05), and this difference becomes extremely apparent (P<0.001) when the dosage reaches 100, 150 and 200 μmol/L, the suppression rate of K562 cell is respectively 16.41%, 29.84% and 46.41%, indicating that monofructosyl-β(2,6)-puerarin can markedly suppress proliferation of human chronmyelogenors leukemia cell strain K562, and the suppression rate increases with the increase of dosage.

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

What is claimed is:

1. A fructosylated puerarin, comprising a structure of Formula (I):

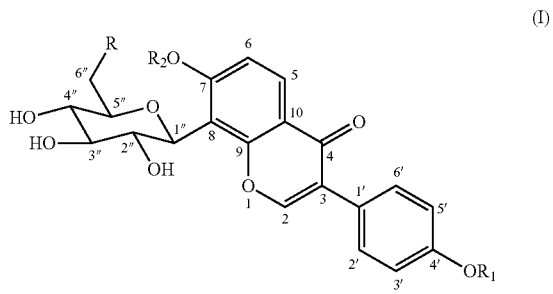

wherein $R_1$ and $R_2$ are independently selected from hydrogen, methyl, ethyl, formoxyl, acetyl, methylamino or sulfonic acid; R is of Formula (II):

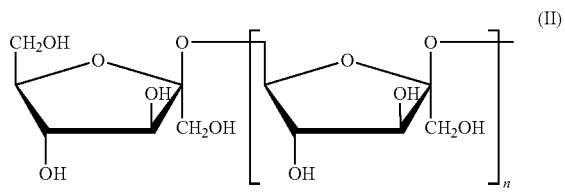

wherein n=0-4.

2. A method of preparing the fructosylated puerarin of claim 1, comprising a step of performing bioconversion of puerarin to fructosylated puerarin using a fermentation liquid or a supernatant of the fermentation liquid having a fructosylation enzymatic activity or using a fructosylation enzyme purified or produced by recombinant gene expression.

3. The method of claim 2, further comprising a step of removing impurities, bacterial cells and bacterial proteins, a step of purification using a resin to afford a fructosylated puerarin fraction, and a step of drying the fructosylated puerarin fraction into rotary evaporation or frozen drying to a form of powder or crystal.

4. The method of claim 2, wherein said fermentation liquid or its supernatant is prepared from fermentation by a microorganism possessing an enzymatic activity for fructosylation.

5. The method of claim 4, wherein said microorganism is Arthrobace nicotianae XM6.

6. The method of claim 2, wherein said fructosylation enzyme purified or produced by recombinant gene expression is beta-D-fructofuranosidase.

7. The method of claim 4, wherein said fermentation is performed in a fermentation medium comprising sucrose 5-80 g/L, peptone 5-50 g/L, $KH_2PO_4$ 0.4-4 g/L, $CaCl_2$ 0.5-5 g/L, and $MnSO_4$ 0.1-2 g/L at pH6-8.

8. The method of claim 7, wherein said fermentation medium comprises sucrose 15 g/L, peptone 25 g/L, $KH_2PO_4$ 2 g/L, $CaCl_2$ 2 g/L, and $MnSO_4$ 0.2 g/L at pH7.5.

9. The method of claim 7, wherein said fermentation is performed at 30° C. in a shake flask oscillating at 240 rpm for 16 hours or in agitating fermentation tank with ventilation at a ventilatory capacity of 4 vvm and a speed of 300 rpm for 6 hours.

10. The method of claim 2, wherein said bioconversion is performed in an aqueous phase or non-aqueous phase with an organic solvent.

11. The method of claim 10, wherein said step of purification using a resin comprises a step of absorbing said fermentation liquid or a supernatant of thereof with AB-8 macroporous resin, removing residual glycosyl donor with an eluent, and then obtaining said fructosylated puerarin via gradient or phase elution.

12. The method of claim 11, wherein said bioconversion is performed in a non-aqueous phase and said step of purification using a resin is conducted after said organic solvent in said fermentation liquid has been removed by a low temperature evaporation process or diluted to below a volumetric ratio of 2%.

13. The method of claim 12, further comprising a step of recovering residual puerarin via elution with 100% methanol or ethanol.

14. A method of treating cardio-cerebrovascular diseases or tumors by administering to a patient a pharmaceutical composition comprising a fructosylated puerarin of claim 1.

15. The fructosylated puerarin of claim 1, which is monofructosyl-(2,6)-puerarin.

16. The fructosylated puerarin of claim 1, which is bifructosyl-(2,6)-puerarin.

17. The fructosylated puerarin of claim 1, which is trifructosyl-(2,6)-puerarin.

18. The fructosylated puerarin of claim 1, which is tetrafructosyl-(2,6)-puerarin.

19. The fructosylated puerarin of claim 1, which is pentafructosyl-(2,6)-puerarin.

* * * * *